(12) United States Patent
Uehara

(10) Patent No.: US 12,423,562 B2
(45) Date of Patent: Sep. 23, 2025

(54) MACHINE LEARNING SYSTEM AND METHOD, INTEGRATION SERVER, INFORMATION PROCESSING APPARATUS, PROGRAM, AND INFERENCE MODEL CREATION METHOD

(71) Applicant: FUJIFILM Corporation, Tokyo (JP)

(72) Inventor: Daiki Uehara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 629 days.

(21) Appl. No.: 17/901,817

(22) Filed: Sep. 1, 2022

(65) Prior Publication Data

US 2023/0004785 A1 Jan. 5, 2023

Related U.S. Application Data

(63) Continuation of application No. PCT/JP2021/012512, filed on Mar. 25, 2021.

(30) Foreign Application Priority Data

Mar. 27, 2020 (JP) ................................ 2020-057929

(51) Int. Cl.
*G06N 3/045* (2023.01)
*G16H 40/20* (2018.01)

(52) U.S. Cl.
CPC ............. *G06N 3/045* (2023.01); *G16H 40/20* (2018.01)

(58) Field of Classification Search
None
See application file for complete search history.

(56) References Cited

U.S. PATENT DOCUMENTS 11,589,174 B2 * 2/2023 Irakoze ................ H04R 25/507
11,804,050 B1 * 10/2023 Milletari ................ G06V 20/64
(Continued)

FOREIGN PATENT DOCUMENTS

JP 2019045929 3/2019
JP 2019526851 9/2019
(Continued)

OTHER PUBLICATIONS

Li et al., "Federated Learning: Challenges, Methods, and Future Directions," Aug. 21, 2019, https://arxiv.org/abs/1908.07873.*
(Continued)

*Primary Examiner* — Ryan Barrett
(74) *Attorney, Agent, or Firm* — JCIPRNET

(57) ABSTRACT

Provided are a machine learning system and method, an integration server, an information processing apparatus, a program, and an inference model creation method capable of suppressing a variation in learning data in federated learning and suppressing a variation in an inference accuracy of a model. The integration server receives an input that designates a data search condition and transmits the designated search condition to a plurality of client terminals. Each client terminal performs searching within a medical institution system to which each terminal belongs and transmits a totalization result of the number of pieces of data that matches the search condition to the integration server. The integration server receives an input that designates the required number of pieces of learning data and distributes the number of pieces of learning data used for learning on each client terminal based on the designated required number and on the received totalization result. The client terminal executes machine learning of a local model to be trained using the data in the medical institution system according to the designated type and number of pieces of learning data (Continued)

and transmits the learning result to the integration server. The integration server integrates the received learning results to update a master model.

20 Claims, 13 Drawing Sheets

(56) References Cited

U.S. PATENT DOCUMENTS

| | | | |
|---|---|---|---|
| 12,072,954 B1* | 8/2024 | Li | G06F 18/2148 |
| 2018/0018590 A1 | 1/2018 | Szeto | |
| 2020/0311300 A1* | 10/2020 | Callcut | G06F 16/256 |
| 2020/0380356 A1 | 12/2020 | Yoshiyama | |
| 2021/0397427 A1* | 12/2021 | Haswell | H04L 63/083 |
| 2022/0058507 A1* | 2/2022 | El-Khamy | G06N 7/01 |
| 2022/0092349 A1* | 3/2022 | Yang | G06T 15/20 |
| 2022/0116764 A1* | 4/2022 | Pezeshki | H04W 72/20 |
| 2022/0164661 A1* | 5/2022 | Uehara | G06N 3/044 |
| 2022/0172844 A1* | 6/2022 | Uehara | G16H 40/67 |
| 2022/0237508 A1* | 7/2022 | Shaloudegi | G06F 17/16 |
| 2022/0237898 A1* | 7/2022 | Uehara | G06N 3/08 |
| 2022/0351039 A1* | 11/2022 | Satheesh Kumar | G06N 3/08 |
| 2022/0366220 A1* | 11/2022 | Roth | H04L 67/34 |
| 2023/0050708 A1* | 2/2023 | Watanabe | G06N 3/08 |
| 2023/0132213 A1* | 4/2023 | Lee | G06N 3/098 706/12 |
| 2023/0186159 A1* | 6/2023 | Antony | G06N 3/098 706/12 |
| 2023/0186167 A1* | 6/2023 | Singla | G06N 3/098 706/12 |
| 2023/0316141 A1* | 10/2023 | Toporek | G16H 10/60 706/12 |
| 2023/0327728 A1* | 10/2023 | Jeon | H04B 17/318 370/329 |
| 2023/0401488 A1* | 12/2023 | Sato | G06N 5/01 |
| 2024/0330706 A1* | 10/2024 | Pompili | G06N 3/045 |

FOREIGN PATENT DOCUMENTS

| | | |
|---|---|---|
| WO | 2011052025 | 5/2011 |
| WO | 2018155232 | 8/2018 |

OTHER PUBLICATIONS

Liu et al., "Projected Federated Averaging with Heterogeneous Differential Privacy," Dec. 1, 2021, Proceedings of the VLDB Endowment, vol. 15, Issue 4, pp. 828-840, https://dl.acm.org/doi/10.14778/3503585.3503592.*

H. Brendan McMahan et al., "Communication-Efficient Learning of Deep Networks from Decentralized Data", arXiv:1602.05629v3, Feb. 2017, pp. 1-11.

Micah J Sheller et al., "Multi-Institutional Deep Learning Modeling Without Sharing Patient Data: A Feasibility Study on Brain Tumor Segmentation", arXiv:1810.04304v2, Oct. 2018, pp. 1-14.

"International Search Report (Form PCT/ISA/210) of PCT/JP2021/012512," mailed on Jun. 8, 2021, with English translation thereof, pp. 1-5.

"Written Opinion of the International Searching Authority (Form PCT/ISA/237) of PCT/ JP2021/012512," mailed on Jun. 8, 2021, with English translation thereof, pp. 1-6.

* cited by examiner

FIG. 2

| PRIMARY DATA | SECONDARY DATA |
|---|---|
| DATA THAT NEEDS IMAGE CAPTURING, WRITING BY DOCTOR, OR LIKE | DATA THAT CAN BE ACQUIRED BY OPERATING AI USING PRIMARY DATA |
| [EXAMPLE]<br><br>CT IMAGE A    COMMENTS ON FINDINGS ASSOCIATED WITH CT IMAGE A | [EXAMPLE]<br><br>PROCESSING RESULT OF LUNG DISEASE REGION EXTRACTION AI EXECUTED FOR CT IMAGE A |
| DATA THAT CANNOT BE AUTOMATICALLY GENERATED | DATA THAT CAN BE AUTOMATICALLY GENERATED |

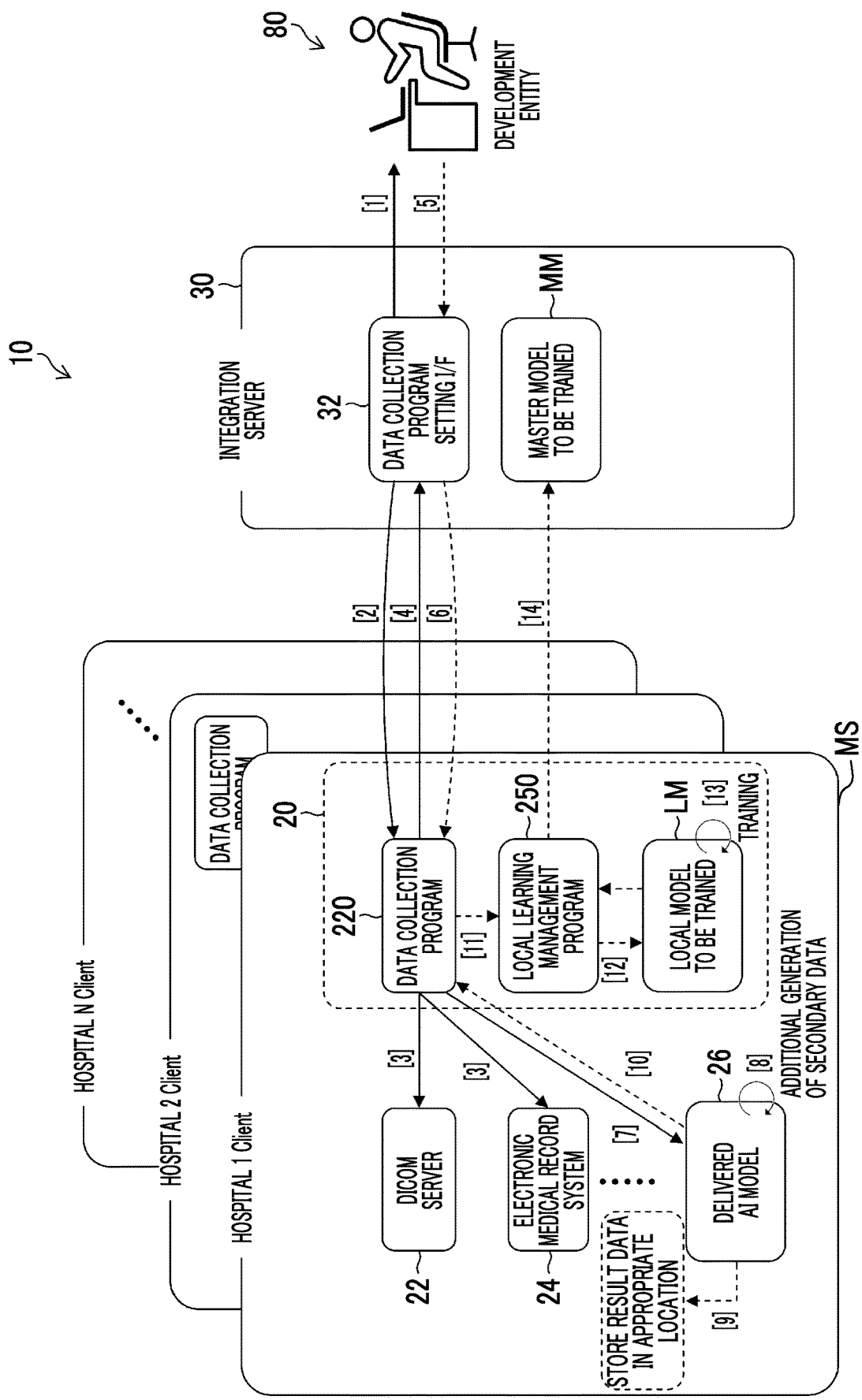

MACHINE LEARNING SYSTEM AND METHOD, INTEGRATION SERVER, INFORMATION PROCESSING APPARATUS, PROGRAM, AND INFERENCE MODEL CREATION METHOD

CROSS-REFERENCE TO RELATED APPLICATIONS

The present application is a Continuation of PCT International Application No. PCT/JP2021/012512 filed on Mar. 25, 2021 claiming priority under 35 U.S.C § 119(a) to Japanese Patent Application No. 2020-057929 filed on Mar. 27, 2020. Each of the above applications is hereby expressly incorporated by reference, in its entirety, into the present application.

BACKGROUND OF THE INVENTION

1. Field of the Invention

The present invention relates to a machine learning system and method, an integration server, an information processing apparatus, a program, and an inference model creation method, and particularly relates to a machine learning technique using a federated learning mechanism.

2. Description of the Related Art

In development of medical artificial intelligence (AI) using deep learning, it is necessary to train an AI model. However, for this learning, it is necessary to extract learning data such as a diagnosis image from a medical institution to an external development site or to an external development server. For this reason, there are few medical institutions that provide the data. Further, even in a case where the data is provided from a medical institution, there is always a privacy-related risk.

On the other hand, in a case where a federated learning mechanism being proposed in H. Brendan McMahan, Eider Moore, Daniel Ramage, Seth Hampson, and Blaise Agüera y Arcas, "Communication-Efficient Learning of Deep Networks from Decentralized Data", arXiv:1602.05629v3 [cs.LG], 28 Feb. 2017 is used, learning is performed on a terminal in which data for training exists, and only a weight parameter of a network model that is a learning result on each terminal is transmitted from a terminal group to an integration server. That is, in federated learning, learning data is not provided to the integration server side, and only data of the learning result on each terminal is provided from the terminal side to the integration server side.

For this reason, learning can be performed without extracting data that requires consideration for privacy to the outside. Thus, federated learning is a technique that has been attracting attention in recent years.

In Micah J Sheller, G Anthony Reina, Brandon Edwards, Jason Martin, and Spyridon Bakas, "Multi-Institutional Deep Learning Modeling Without Sharing Patient Data: A Feasibility Study on Brain Tumor Segmentation", arXiv: 1810.04304v2 [cs.LG], 22 Oct. 2018, a result of an example in which federated learning is applied to development of a medical AI is reported.

SUMMARY OF THE INVENTION

In a case where federated learning is used for development of a medical AI, it is not necessary to extract data such as a diagnosis image. However, contents of the data held by each medical institution vary, and learning environments are different for each client. As a result, results of learning performed by each client also vary.

For this reason, in a case where an AI model is trained by randomly selecting the learning data in a plurality of medical institutions, a variation occurs in inference accuracy of the AI model. According to the content reported in Micah J Sheller, G Anthony Reina, Brandon Edwards, Jason Martin, and Spyridon Bakas, "Multi-Institutional Deep Learning Modeling Without Sharing Patient Data: A Feasibility Study on Brain Tumor Segmentation", arXiv: 1810.04304v2 [cs.LG], 22 Oct. 2018, all of data prepared in a verification environment are used as they are as the learning data for training a local model. This still means that there is no method of collecting data for training other than random sampling in actual operation. In a case where data is extracted by random sampling, there may be a variation in the data to be used for learning. Thus, there is a concern that the variation occurs in the inference accuracy of the AI model to be created.

The present invention has been made in view of such circumstances, and an object of the present invention is to provide a machine learning system and method, an integration server, an information processing apparatus, a program, and an inference model creation method capable of suppressing a variation in an inference accuracy of an AI model, which is caused by randomly selected learning data in a case where a federated learning mechanism is implemented in which the AI model can be trained without extracting personal information such as a diagnosis image that requires consideration for privacy from a medical institution to the outside.

A machine learning system according to one aspect of the present disclosure comprises a plurality of client terminals and an integration server. Each of the plurality of client terminals is a terminal installed in a medical institution system of each of a plurality of medical institutions. Each of the client terminals includes a first processor and a first computer-readable medium on which a first program executed by the first processor is recorded. The first processor performs, according to a command of the first program, processing including acquiring a search condition of data from the integration server, searching for data that matches the search condition from within the medical institution system to which the client terminal belongs and totaling search results, transmitting a totalization result indicating the number of pieces of the data that matches the search condition to the integration server, receiving distribution information in which a type and the number of pieces of learning data used for learning at the client terminal are designated, executing machine learning of a local model to be trained in accordance with an instruction of the distribution information using data in the medical institution system to which the client terminal belongs as the learning data, and transmitting a learning result of the local model to the integration server. The integration server includes a second processor and a second computer-readable medium on which a second program executed by the second processor is recorded. The second processor performs, according to a command of the second program, processing including storing a master model to be trained on the second computer-readable medium, receiving an input that designates the search condition in a case where the data in the medical institution system is searched for, transmitting the designated search condition to the plurality of client terminals, receiving the totalization result indicating the number of pieces of data that matches the search condition from each of the client terminals, receiving an input that designates the required number of pieces of learning data to be used for learning, distributing the number of pieces of the learning data used for learning at each of the client terminals based on the designated required number of pieces of the learning data and on the received totalization result, transmitting, to each of the client terminals, the distribution information including the designation of the number of pieces of the learning data distributed according to each of the client terminals, synchronizing the local model of each client terminal side with the master model before the local model is trained at each of the plurality of client terminals, receiving each of the learning results from the plurality of client terminals, and integrating the received learning results to update the master model.

According to this aspect, it is possible to set the data search condition from the integration server to search for the data in the medical institution system of each medical institution and thus ascertain a possession situation of data for each medical institution in the integration server. Further, according to this aspect, it is possible to designate the type and number of pieces of learning data to be used for learning on each client terminal from the integration server by receiving the totalization result of the number of pieces of data that matches the search result and thus suppress a variation in the learning data. Accordingly, it is possible to suppress a variation in the inference accuracy of the model obtained by performing the learning.

The term "plurality of client terminals" may be an unspecified large number of client terminals. The client terminal may be configured to include a data storage device that stores the data in the medical institution system, or the data storage device and the client terminal may be separate devices.

In the machine learning system according to another aspect of the present disclosure, the second processor may further issue a notification notifying that the required number is satisfied at a stage where a total number of pieces of the data that matches the search condition is equal to or larger than the required number.

In the machine learning system according to still another aspect of the present disclosure, the first processor may have authority to execute a third program that generates new secondary data using primary data in the medical institution system. The second processor may perform, in a case where a total number of pieces of the data that matches the search condition is less than the required number and the data that matches the search condition is obtainable by operating the third program, processing including distributing the number of pieces of additional data requesting additional data generation to each of the client terminals, and transmitting, to each of the client terminals, additional generation distribution information including designation of the number of pieces of the additional data distributed according to each of the client terminals. The first processor may execute the third program based on the additional generation distribution information to newly generate the secondary data.

In the machine learning system according to still another aspect of the present disclosure, the first processor may start training of the local model in a case where the generation of the secondary data of the designated number of pieces of the additional data is completed.

In the machine learning system according to still another aspect of the present disclosure, the third program may include a trained model in which the secondary data is output by inputting the primary data.

In the machine learning system according to still another aspect of the present disclosure, each of the plurality of client terminals may be a terminal installed in a medical institution network of a different medical institution.

In the machine learning system according to still another aspect of the present disclosure, the integration server may be installed in a medical institution network or outside the medical institution network.

In the machine learning system according to still another aspect of the present disclosure, the learning result transmitted from the client terminal to the integration server may include a weight parameter of the local model after learning.

In the machine learning system according to still another aspect of the present disclosure, data to be searched for by the search condition may include at least one type of data of a two-dimensional image, a three-dimensional image, a moving image, time-series data, or document data.

In the machine learning system according to still another aspect of the present disclosure, the document data may include comments on findings of an electronic medical record.

In the machine learning system according to still another aspect of the present disclosure, models to be trained of each of the local model and the master model may be trained such that comments on findings corresponding to an input image are output, using a combination of an image and comments on findings associated with the image as the learning data.

In the machine learning system according to still another aspect of the present disclosure, models to be trained of each of the local model and the master model may be configured by using a neural network.

An appropriate network model is applied according to a type of the learning data and a type of data that is input in the inference.

In the machine learning system according to still another aspect of the present disclosure, the data used as the learning data may include a two-dimensional image, a three-dimensional image, or a moving image. Models to be trained of each of the local model and the master model may be configured by using a convolutional neural network.

In the machine learning system according to still another aspect of the present disclosure, the data used as the learning data may include time-series data or document data. Models to be trained of each of the local model and the master model may be configured by using a recurrent neural network.

A machine learning method according to still another aspect of the present disclosure is a machine learning method in which a plurality of client terminals and an integration server are used. The method comprises, via each of the plurality of client terminals, which are installed in a medical institution system of each of a plurality of medical institutions, storing a master model to be trained in the integration server, via the integration server, receiving an input that designates a search condition in a case where data in the medical institution system is searched for and transmitting the designated search condition to the plurality of client terminals, via the client terminal, acquiring the search condition from the integration server, searching for data that matches the search condition from within the medical institution system to which the client terminal belongs and totaling search results, and transmitting a totalization result indicating the number of pieces of the data that matches the search condition to the integration server, via the integration server, receiving the totalization result indicating the number of pieces of data that matches the search condition from each of the client terminals, receiving an input that designates the required number of pieces of learning data to be used for learning, distributing the number of pieces of the learning data used for learning at each of the client terminals based on the designated required number of pieces of the learning data and on the received totalization result, transmitting, to each of the client terminals, distribution information including the designation of the number of pieces of the learning data distributed according to each of the client terminals, and synchronizing the local model of each client terminal side with the master model before the local model is trained at each of the plurality of client terminals, via the client terminal, receiving the distribution information in which a type and the number of pieces of learning data used for learning at the client terminal are designated, executing machine learning of a local model to be trained in accordance with an instruction of the distribution information using data in the medical institution system to which the client terminal belongs as the learning data, and transmitting a learning result of the local model to the integration server, and, via the integration server, receiving each of the learning results from the plurality of client terminals, and integrating the received learning results to update the master model.

An information processing apparatus according to still another aspect of the present disclosure is used as a client terminal connected to an integration server via a communication line and is a terminal installed in a medical institution system of a medical institution. The information processing apparatus comprises a first processor and a first computer-readable medium on which a first program executed by the first processor is recorded. The first processor performs, according to a command of the first program, processing including acquiring a search condition of data from the integration server, searching for data that matches the search condition from within the medical institution system to which the client terminal belongs and totaling search results, transmitting a totalization result indicating the number of pieces of the data that matches the search condition to the integration server, receiving distribution information in which a type and the number of pieces of learning data used for learning at the client terminal are designated, executing machine learning of a local model to be trained in accordance with an instruction of the distribution information using data in the medical institution system to which the client terminal belongs as the learning data, and transmitting a learning result of the local model to the integration server.

In the information processing apparatus according to still another aspect of the present disclosure, the first processor may have authority to execute a third program that generates new secondary data using primary data in the medical institution system and execute the third program according to the number of pieces of additional data designated by the integration server to newly generate the secondary data.

A program according to still another aspect of the present disclosure is a program for causing a first computer to function as a client terminal connected to an integration server via a communication line. The program causes the first computer to realize a function of acquiring a search condition of data from the integration server, a function of searching for data that matches the search condition from within a medical institution system to which the client terminal belongs and totaling search results, a function of transmitting a totalization result indicating the number of pieces of the data that matches the search condition to the integration server, a function of receiving distribution information in which a type and the number of pieces of learning data used for learning at the client terminal are designated, a function of executing machine learning of a local model to be trained in accordance with an instruction of the distribution information using data in the medical institution system to which the client terminal belongs as the learning data, and a function of transmitting a learning result of the local model to the integration server.

An integration server according to still another aspect of the present disclosure is an integration server connected to a plurality of client terminals via a communication line. The integration server comprises a second processor and a second computer-readable medium on which a second program executed by the second processor is recorded. The second processor performs, according to a command of the second program, processing including storing a master model to be trained on the second computer-readable medium, receiving an input that designates a search condition in a case where data in a medical institution system to which each of the plurality of client terminals belongs is searched for, transmitting the designated search condition to the plurality of client terminals, receiving a totalization result indicating the number of pieces of the data that matches the search condition from each of the client terminals, receiving an input that designates the required number of pieces of learning data to be used for learning, distributing the number of pieces of the learning data used for learning at each of the client terminals based on the designated required number of pieces of the learning data and on the received totalization result, transmitting, to each of the client terminals, distribution information including the designation of the number of pieces of the learning data distributed according to each of the client terminals, synchronizing a local model of each client terminal side with the master model before the local model is trained at each of the plurality of client terminals, receiving a learning result of each of the local models from the plurality of client terminals, and integrating the received learning results to update the master model.

In the integration server according to still another aspect of the present disclosure, each of the client terminals may have authority to execute a third program that generates new secondary data using primary data in the medical institution system. The second processor may perform, in a case where a total number of pieces of the data that matches the search condition is less than the required number and the data that matches the search condition is obtainable by operating the third program, processing including distributing the number of pieces of additional data requesting additional data generation to each of the client terminals and transmitting, to each of the client terminals, additional generation distribution information including designation of the number of pieces of the additional data distributed according to each of the client terminals.

A program according to still another aspect of the present disclosure is a program for causing a second computer to function as an integration server connected to a plurality of client terminals via a communication line. The program causes the second computer to realize a function of storing a master model to be trained, a function of receiving an input that designates a search condition in a case where data in a medical institution system to which each of the plurality of client terminals belongs is searched for, a function of transmitting the designated search condition to the plurality of client terminals, a function of receiving a totalization result indicating the number of pieces of the data that matches the search condition from each of the client terminals, a function of receiving an input that designates the required number of pieces of learning data to be used for learning, a function of distributing the number of pieces of the learning data used for learning at each of the client terminals based on the designated required number of pieces of the learning data and on the received totalization result, a function of transmitting, to each of the client terminals, distribution information including the designation of the number of pieces of the learning data distributed according to each of the client terminals, a function of synchronizing a local model of each client terminal side with the master model before a local model is trained at each of the plurality of client terminals, a function of receiving a learning result of each of the local models from the plurality of client terminals, and a function of integrating the received learning results to update the master model.

A method for creating an inference model according to still another aspect of the present disclosure is a method of creating an inference model by performing machine learning using a plurality of client terminals and an integration server. The inference model creation method comprises, via each of the plurality of client terminals, which are installed in a medical institution system of each of a plurality of medical institutions, storing a master model to be trained in the integration server, via the integration server, receiving an input that designates a search condition in a case where data in the medical institution system is searched for, and transmitting the designated search condition to the plurality of client terminals, via the client terminal, acquiring the search condition from the integration server, searching for data that matches the search condition from within the medical institution system to which the client terminal belongs and totaling search results, and transmitting a totalization result indicating the number of pieces of the data that matches the search condition to the integration server, via the integration server, receiving the totalization result indicating the number of pieces of data that matches the search condition from each of the client terminals, receiving an input that designates the required number of pieces of learning data to be used for learning, distributing the number of pieces of the learning data used for learning at each of the client terminals based on the designated required number of pieces of the learning data and on the received totalization result, transmitting, to each of the client terminals, distribution information including the designation of the number of pieces of the learning data distributed according to each of the client terminals, and synchronizing the local model of each client terminal side with the master model before the local model is trained at each of the plurality of client terminals, via the client terminal, receiving the distribution information in which a type and the number of pieces of learning data used for learning at the client terminal are designated, executing machine learning of a local model to be trained in accordance with an instruction of the distribution information using data in the medical institution system to which the client terminal belongs as the learning data, and transmitting a learning result of the local model to the integration server, and, via the integration server, receiving each of the learning results from the plurality of client terminals, and creating, by integrating the received learning results to update the master model, an inference model having higher inference accuracy than the master model before the update.

The inference model creation method is understood as an invention of a method of producing the inference model. The term "inference" includes concepts of prediction, estimation, classification, and determination. The inference model may be paraphrased as "AI model". The inference model may be a model that generates data.

According to the aspects of the present invention, a mechanism is provided in which the possession situation of data in each medical institution system can be checked by designating the search condition from the integration server.

According to the aspects of the present invention, since the type and number of pieces of learning data used for learning on each client terminal can be designated from the integration server for each medical institution, it is possible to suppress the variation in the learning data and thus suppress the variation in the inference accuracy of the AI model obtained by learning.

BRIEF DESCRIPTION OF THE DRAWINGS

FIG. 2 is a diagram for describing a type of learning data.

FIG. 3 is a conceptual diagram showing the outline of the operation of the machine learning system in a case where the total number of pieces of learning data is insufficient.

DESCRIPTION OF THE PREFERRED EMBODIMENTS

Hereinafter, preferred embodiments of the present invention will be described with reference to the accompanying drawings.

<<Outline of Machine Learning System>>

Figure 1:
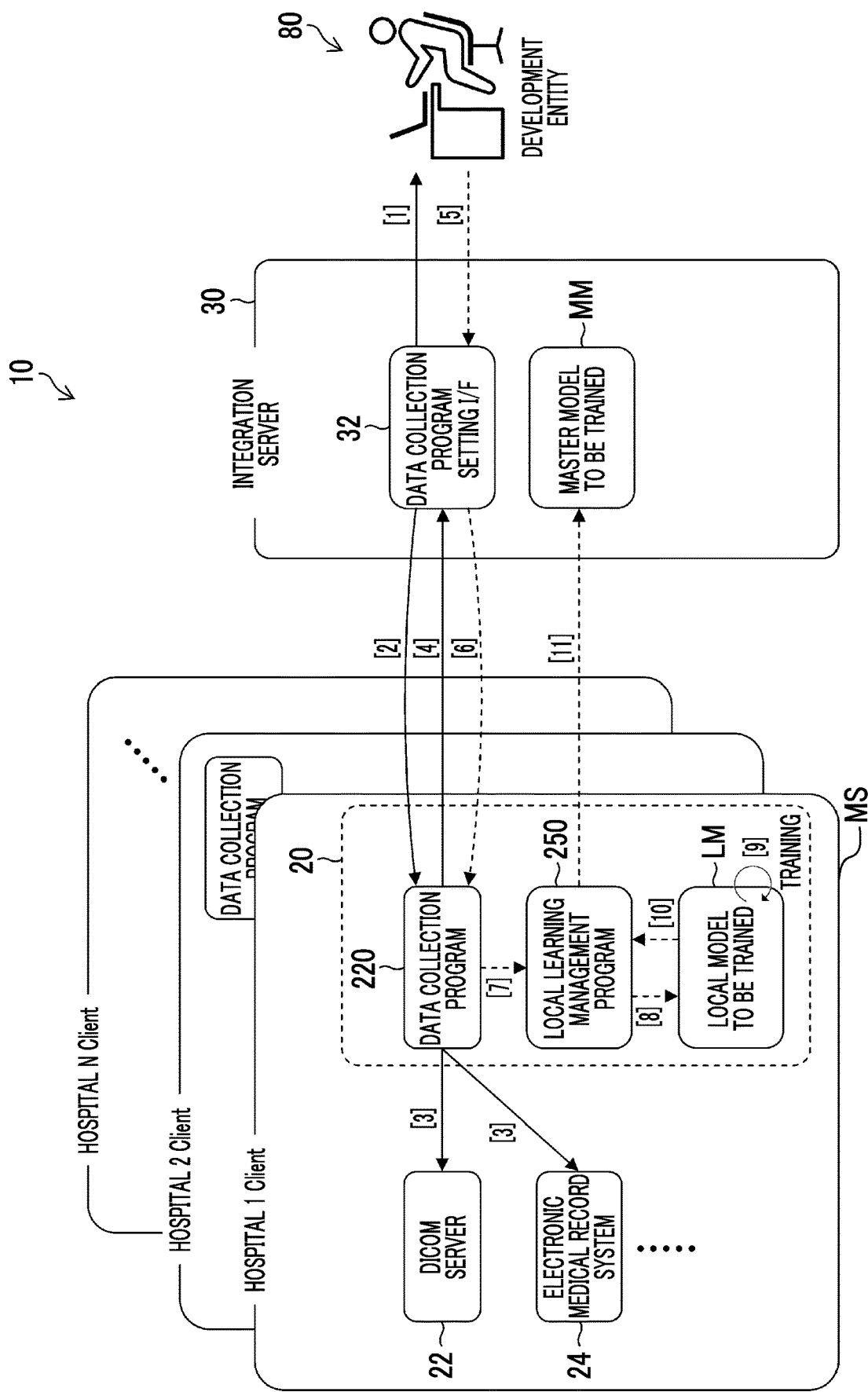
FIG. 1 is a conceptual diagram showing an outline of an operation of a machine learning system according to an embodiment of the present invention.

FIG. 1 is a conceptual diagram showing an outline of a machine learning system 10 according to an embodiment of the present invention. The machine learning system 10 is a computer system that performs machine learning using a federated learning mechanism. Federated learning is sometimes referred to as "federation learning", "distribution learning", "cooperative learning", or "combination learning".

The machine learning system 10 includes a terminal 20, which is installed on a network in each medical institution of a plurality of medical institutions, and an integration server 30. The terminal 20 refers to a computing resource existing in a network in which data in a medical institution can be safely accessed, and the terminal 20 may not physically exist in the medical institution. That is, the terminal 20 in each medical institution may be a physical machine or a virtual machine, and a specific form thereof is not limited. The terminal 20 is an example of "client terminal" according to the present disclosure. A computer network in a medical institution is referred to as "medical institution network".

The terminal 20 is assumed to exist for each data group for training an AI model to be trained. The term "for each data group" described herein may be understood as "for each medical institution" that holds a data group to be used for training the AI model. That is, one terminal 20 is assumed to exist approximately for one medical institution. The computer system constructed on the medical institution network of each medical institution is referred to as a medical institution system MS. A representative example of the medical institution is "hospital".

The display of "Hospital 1 Client", "Hospital 2 Client", . . . , "Hospital N Client" shown in FIG. 1 represents the medical institution system MS of each medical institution. A number after "hospital" is an index as an identification number that identifies each medical institution (hospital). The index number may be understood as a client identification (ID) number of the terminal 20 or may be understood as "client ID number" of a medical institution having the medical institution system MS including the terminal 20.

In addition to the terminal 20, each medical institution system MS includes an information system that stores and manages various pieces of medical information in the medical institution, such as a digital imaging and communication in medicine (DICOM) server 22 and an electronic medical record system 24. The DICOM server 22 is a server that operates according to a DICOM specification. The DICOM server 22 is a computer that stores and manages various pieces of data including medical images, such as a CT image and an MM image, and comprises a large-capacity external storage device and software for database management.

The electronic medical record system 24 is a computer system that creates, edits, stores, and manages an electronic medical record. The electronic medical record system 24 comprises a large-capacity external storage device that stores electronic medical record data and the like and software for database management.

In FIG. 1, the display of "dots" shown below the electronic medical record system 24 indicates that other information systems (not shown) may exist. Other information systems may be any system that manages data in the medical institution and that can be searched for, and contents of the data are not limited.

The terminal 20 of each medical institution includes a data collection program 220 and a local learning management program 250. The data collection program 220 searches for and collects data used for learning from the medical institution network in accordance with an instruction from the integration server 30. The data collection program 220 has a function of recording which data in the medical institution system MS is data that matches a search condition designated by a development entity 80 of the AI model (master model), a function of totaling the number of pieces of data that matches the designated search condition, and a function of transmitting the totaled number of pieces of data to the integration server 30. The search condition used by the data collection program 220 is provided by the integration server 30.

Learning target data to be searched for according to the search condition may be any data stored in the system to which the data collection program 220 in each terminal 20 is permitted to connect. For example, the learning target data to be searched for may be electronic medical record data, a two-dimensional medical image, a three-dimensional medical image, a moving image, a combination of comments on findings of the electronic medical record and the two-dimensional image, a combination of the comments on findings of the electronic medical record and the three-dimensional image, or the like.

The local learning management program 250 is a client program for the distribution learning and performs training processing on a local model to be trained LM by using local data stored in the medical institution system MS as learning data, in cooperation with the data collection program 220. The local data means data stored in the medical institution system MS to which the terminal 20 belongs.

The local learning management program 250 has functions of starting training of the local model to be trained LM, transmitting a learned weight parameter file to the integration server 30, and the like. That is, the local learning management program 250 has functions of synchronizing a master model to be trained MM before training with the local model to be trained LM, starting the local learning, setting an end condition of the local learning, and transmitting a learning result of the local learning to the integration server 30 in a case where the local learning ends.

The local model to be trained LM is the AI model to be trained and performs the learning by using each piece of local data in each medical institution. The local model to be trained LM may be simply described as "local model". The training of the local model LM using the local data is referred to as "local learning". The local model LM is synchronized with the master model to be trained MM of the integration server 30 before the learning starts.

The integration server 30 comprises a data collection program setting interface (I/F) 32 and the master model to be trained MM. The term "I/F" is an abbreviation for "interface". The data collection program setting interface 32 is an interface for setting various conditions and the like, such as what kind of data is desired to be searched for by the data collection program 220 of each medical institution system MS and what kind of data type and how many pieces of data are used for learning. In a case where a plurality of types of data are used for learning, the number of pieces of data for each data type used for learning is set.

The data collection program 220 developed in the terminal 20 of each medical institution searches for and totals, for each data type, the number of pieces of data that matches the search condition instructed from the integration server 30 side or the like in the medical institution system MS to which the terminal 20 belongs and transmits the totalization result to the integration server 30.

The master model to be trained MM is a master model to be trained this time. The master model to be trained MM represents a learning model for obtaining an AI model that is desired to be released as a product. The master model to be trained MM may be simply described as "master model".

The integration server 30 may be on a computer network on which the development entity 80 of the AI model has access rights, and a form of the server may be a physical server, a virtual server, or the like. The integration server 30 may be installed in the medical institution network or may be installed outside the medical institution network. For example, the integration server 30 may be installed at a company that is located geographically away from the medical institution and that develops medical AI or may be installed on the cloud.

The development entity 80 represents a company or the like that is trying to train the master model to be trained MM in order to commercialize the AI model or to further improve the performance of the existing AI model. The term development entity 80 also includes a developer, an operator, and the like belonging to the company and the like.

The integration server 30 ascertains a possession situation of data that can be used as the learning data for each medical institution through the data collection program setting interface 32 and distributes the number of pieces of learning data used for the local learning on each terminal 20 of the plurality of medical institutions such that the required number of pieces of learning data for the entire learning is secured. At each medical institution, the local learning is executed by using the learning data having the number of pieces of data designated from the integration server 30. The integration server 30 receives respective learning results from the terminals 20 of the plurality of medical institutions, integrates the learning results, and updates the master model MM.

<<Example of AI Model>>

The master model MM and the local model LM are collectively referred to as "model to be trained". The model to be trained may be, for example, an AI model for medical image diagnosis assuming application to a computer aided detection/diagnosis (CAD) system. The term "CAD" includes concepts of both computer aided detection (CADe) and computer aided diagnosis (CADx). Further, the model to be trained may be, for example, an AI model for report creation support that supports creation of a document such as the comments on findings. The term "comments on findings" includes a concept of diagnostic report. The AI model is configured by using, for example, a hierarchical multi-layer neural network. In the local model LM, a network weight parameter is updated by deep learning using local data LD as learning data. The weight parameter includes a filter coefficient (weight of a connection between nodes) of a filter used for processing of each layer and a bias of a node.

The term "neural network" is a mathematical model for information processing that simulates a mechanism of a brain-nervous system. Processing using the neural network can be realized by using a computer. A processing unit including the neural network may be configured as a program module.

As a network structure of the neural network used for learning, an appropriate network structure is employed according to a type of data used for input. The AI model for medical image diagnosis may be configured by using, for example, various convolutional neural networks (CNNs) having a convolutional layer. The input data to the AI model may be, for example, medical images such as a two-dimensional image, a three-dimensional image, and a moving image. An output from the AI model may be, for example, information indicating a position of a disease region (lesion portion) or the like in the image, information indicating a class classification such as a disease name, or a combination of the pieces of information.

The AI model that handles time-series data, document data, or the like may be configured by using, for example, various recurrent neural networks (RNNs). The time-series data includes, for example, electrocardiogram waveform data. The document data includes, for example, the comments on findings created by a doctor.

<<Outline of Machine Learning Method>>

[1] to [11] in FIG. 1 represent the series of flows from the searching and collection of data used for learning to the local learning and further integration into the master model MM. In the following description, operations indicated by arrows and the like numbered [1] to [11] are expressed as operation [1], operation [2], . . . , operation [11]. The machine learning system 10 according to the present embodiment operates according to procedures 1 to 11 shown below.

<Procedure 1> The integration server 30 comprises the data collection program setting interface 32 for the development entity 80 making a training plan of the AI model to designate the search condition. The development entity 80 can designate the search condition through the data collection program setting interface 32.

The operation [1] in FIG. 1 represents an operation in which the development entity 80 designates the search condition. The search condition is, for example, a condition such as totaling the number of pieces of data in which a ground glass-like shadow is detected as a result of lung CAD execution. This condition can be searched for by inquiring of a database that stores an AI processing result in each medical institution or the like. The lung CAD is an example of an AI processing module using a trained AI model that outputs a detection result of a lung disease region and/or a recognition result of a disease name and the like, using a computed tomography (CT) image of the lung as input data, for example. The term "trained AI model" here is an AI model that has already been delivered (completed) as a product. Hereinafter, such a trained AI model will be described as "delivered AI model". The AI processing module for medical use is not limited to lung CAD and may include various types such as brain CAD and gastrointestinal CAD. The brain CAD outputs a detection result of a disease region and/or a recognition result of a disease name and the like, using a magnetic resonance imaging (Mill) image of the brain as input data, for example. The gastrointestinal CAD outputs a detection result of a disease region (lesion) and/or a recognition result of a disease name and the like, using an endoscopic image of a digestive system such as a stomach and/or an intestine as input data, for example.

<Procedure 2> As the search condition used by the data collection program 220, for example, structural data such as JavaScript object notation (JSON) is provided as a search condition setting file. The term "JavaScript" is a registered trademark. The operation [2] in FIG. 1 represents that the search condition setting file is provided to the data collection program 220.

<Procedure 3> The data collection program 220 reads the search condition setting file to search for data from a system that stores data that can be the learning target, such as the DICOM server 22 and/or the electronic medical record system 24, in accordance with an instruction of the search condition setting file. The operation [3] in FIG. 1 represents processing of searching for the data via the data collection program 220.

The search condition setting file does not have to be a structural data file and may be any data having a format such as providing a search destination which the data collection program 220 searches for and a plurality of parameters or a single parameter necessary for constructing a search query to the search destination.

The search condition may be a single search condition such as only the data in the DICOM server 22 in which a search target stores an image inspection result, or may be a search condition that is extended over a plurality of systems in the medical institution such as searching for the electronic medical record data of a patient having a finding of interstitial pneumonia in the electronic medical record system 24 and a test result image associated with the electronic medical record data.

<Procedure 4> The data collection program 220 stores a location of data that matches the search condition in a data storage unit (search result storage unit) such as a database, totals the number of pieces of data, and transmits the totalization result to the integration server 30. Only the number of pieces of data is transmitted here. The description "only the number of pieces of data" here means that the data itself that matches the search result, such as an image and electronic medical record data that satisfy the search condition, is not transmitted, but the information on the number of pieces of data that matches the search condition is transmitted. The operation [4] in FIG. 1 represents that the totalization result of the number of pieces of data is transmitted to the integration server 30 and that the integration server 30 receives the totalization result.

<Procedure 5> The integration server 30 receives the totalization result from the data collection program 220 and stores the totalization result in a data storage unit (totalization result storage unit) such as a database.

<Procedure 6> The development entity 80 planning to train the AI model sets how many pieces of data that matches the designated search condition are required, through the data collection program setting interface 32 of the integration server 30. For example, the development entity 80 sets the number of pieces of data required for learning, such as a need for 1,000 pieces of data in which the ground glass-like shadow is detected as a result of the lung CAD execution. The operation [5] in FIG. 1 represents an input work in which the development entity 80 sets the required number of pieces of data (required number).

<Procedure 7> The integration server 30 distributes how many pieces of data are required to be used for learning for the terminal 20 of each medical institution based on the search condition of the data necessary for learning and on the required number of the data and transmits the distribution information to the data collection program 220 existing in the medical institution system MS of each medical institution. The operation [6] in FIG. 1 represents the transmission of the distribution information. The distribution described herein means, for example, in a case where the need for 1,000 pieces of data in which the ground glass-like shadow is detected as a result of the lung CAD execution is input to the integration server 30, that the number of pieces of data is assumed to be assigned to each medical institution such as 100 cases for a client of a hospital A, 46 cases for a hospital B, . . . , some cases for a hospital C, and the like.

An upper limit is preferably set for the number of pieces of data to be distributed to each medical institution. In the distribution to each medical institution decided by the integration server 30, the number of pieces of data used for the local learning at each medical institution is set, for example, up to 100 at maximum for one medical institution. In this case, a form may be employed in which a distribution rule is set such that up to 100 pieces of learning data are distributed to be used for learning in a case where the number of pieces of learning data that matches the search condition is 100 or more in a certain medical institution and such that 46 pieces of learning data are distributed to be used for learning in a case where the number of pieces of learning data that matches the search condition is less than 100, for example, the medical institution has only 46 pieces of learning data that matches the search condition, and the number of pieces of data used for learning in each medical institution is distributed until the required number of pieces of data (for example, 1,000) is reached. The distribution rule is not limited to the above example.

<Procedure 8> The data collection program 220 that has received the number of pieces of data that matches the search condition to be used for learning from the integration server 30, as necessary, moves the data that matches the condition to a data storage location where the local learning management program 250 can read the data as the learning data and then activates the local learning management program 250 to start the training of the local model to be trained (local learning model) LM. The operation [7] in FIG. 1 represents that the local learning management program 250 is activated, and the operation [8] represents that the training of the local model to be trained LM is started.

Hereafter, the data used for learning will be identical until the setting is changed or until the training of the master model MM in the integration server 30 is completed. A ring-shaped arrow shown as the operation [9] in FIG. 1 represents that the training is performed on the local model LM.

<Procedure 9> The local learning management program 250 transmits the learned weight parameter to the integration server 30 after the training of the local model LM is completed. The integration server 30 integrates learned weight parameters acquired from the terminal 20 in each medical institution and updates the master model to be trained MM. The operation [10] in FIG. 1 represents that the local learning management program 250 acquires the learned weight parameter of the local model LM after the training is completed, and the operation [11] represents that the learned weight parameter is transmitted to the integration server 30.

The learning completion condition of the local model LM may be a condition that ends after a designated number of iterations, a condition that data for verification is held in the medical institution network, correct answer data shown in the data for verification is compared with an inference result of the model LM to calculate an inference accuracy, and the training is performed until a designated ratio of accuracy improvement is achieved, or a condition that a time limit is set and that the training is performed within the time limit.

<Procedure 10> Hereafter, the training of the local learning model and the integration of the weight parameters of the local learning model in the integration server 30 are repeated until the inference accuracy of the master model MM reaches the desired accuracy.

The flow described in procedures 1 to 10 above is an example in which the total number of pieces of data (total number) that matches the search condition is equal to or larger than the number of pieces of data required for learning and is a flow in a case where the total number of pieces of learning data is sufficient. However, a state is assumed in actual operation where the number of pieces of data required for learning is not sufficient.

<<Countermeasure in Case where Total Number of Pieces of Learning Data is Insufficient>>

Hereinafter, a specific example of behavior of the system in a case where the total number of pieces of learning data is insufficient for the required number will be described. Prior to the description, necessary prerequisites are described below.

FIG. 2 is a diagram for describing a type of learning data. Regarding the type of data used for learning (learning data), "primary data" and "secondary data" are defined as follows.

The term "primary data" is defined as data that cannot be automatically generated systematically, such as an image that cannot be generated unless a patient is imaged by using a modality, such as an X-ray imaging apparatus or an MRI apparatus, or comments on findings that cannot be generated unless written by a doctor.

On the other hand, "secondary data" is defined as data that can be automatically generated systematically, such as data obtained by operating lung disease region extraction AI for an image or the like that has already been captured. The secondary data is data that can be generated by a computer using the primary data.

FIG. 2 shows, as an example of the primary data, a CT image A and comments on findings associated with the CT image A. The CT image A is an image captured by a CT apparatus. The comments on findings associated with the CT image A are comments on findings written by the doctor who made a diagnosis using the CT image A. The term "associated" means "correlated". As an example of the secondary data, a processing result of the lung disease region extraction AI executed to the CT image A is shown. The data of this processing result may be, for example, a bounding box and/or a segmentation image showing a lung disease region extracted from the CT image A.

The following assumptions are made as a combination of the model to be trained as the local model LM and the master model MM described with reference to FIG. 1 and the type of the learning data used for learning.

[Assumption A] A case where the training of the model to be trained is performed by using only the primary data as learning data, such as a combination of the CT image A and the comments on findings associated with the CT image A, as described in the left column of FIG. 2.

[Assumption B] A case where the training of the model to be trained is performed by using, as learning data, a combination of the primary data of the CT image A and the comments on findings associated with the CT image A and the secondary data such as the processing result of the lung disease region extraction AI obtained by operating the delivered (completed) AI model to the CT image A as described in the left and right columns of FIG. 2.

[Assumption C] A case where the training of the model to be trained is performed by using only the secondary data as learning data, as described in the right column of FIG. 2.

Under the above assumptions, an example of the operation in the machine learning system 10 in a case where the total number of pieces of data required for learning is insufficient will be described below.

FIG. 3 is a conceptual diagram showing an outline of the operation of the machine learning system 10 in a case where the total number of pieces of learning data is insufficient. The configuration shown in FIG. 3 will be described focusing on differences from FIG. 1.

The development entity 80 knows how many pieces of data that matches the set search condition exist in total through the system in a flow of operations [1] to [4] of FIG. 3. The operations up to [1] to [4] are performed in the same flow as <Procedure 1> to <Procedure 4> described above.

The development entity 80 knows that, for example, 100 pieces of data that matches the search condition exist through the data collection program setting interface 32. However, a state is assumed in which the development entity 80 wants to actually use 200 pieces of data for learning, and 100 pieces of data required for learning are insufficient. In such a case, since a possible response of the development entity 80 differs depending on which assumption case of the above assumptions A, B, and C is employed for the data required for learning, a countermeasure operation will be described for each assumption case.

[Case of Assumption A]

In a case where the learning data is insufficient in the learning that uses only the primary data as the learning data as in Assumption A, the development entity 80 needs to wait until the necessary data is generated by each medical institution. In this case, it is troublesome for the development entity 80 itself to search and check whether the required number of pieces of data has been collected each time. Therefore, there is a preferable configuration in which the system of the integration server 30 is set to be notified at a stage where the total number of pieces of the data that matches the search condition exceeds 200 and in which the system notifies the development entity 80 as soon as the condition of the required number of pieces of data is met.

[Case of Assumption B]

In a case where the primary data and the secondary data are used as the learning data as in the case of assumption B and in a case where there is an insufficiency of 100 pieces of learning data as a whole since there are 200 or more pieces of primary data but only 100 pieces of secondary data, the secondary data can be automatically generated programmatically. Therefore, the development entity 80 instructs the system to additionally generate the secondary data. A flow from the instruction for the additional generation to the actual generation of additional secondary data is described below.

In an operation [5] in FIG. 3, the development entity 80 designates how many pieces of result data generated from which delivered AI model 26 is required via the data collection program setting interface 32.

The data collection program setting interface 32 distributes an execution condition of the additional generation designated in the operation [5] in FIG. 3 to the data collection program 220 in each medical institution. An operation [6] in FIG. 3 represents a flow of distribution related to this additional generation. The distribution here is performed in a case where 100 additional execution results of the delivered AI model 26 are desired as a whole. For example, assignment for sharing work of addition processing, such as execution of the additional generation processing for 10 execution results in each facility in a case where there are 10 medical institutions, is assumed to be performed.

The data collection program 220 of each medical institution that has received the execution condition by the operation [6] causes the delivered AI model 26 that matches the execution condition to execute the processing for 10 execution results. An operation [7] in FIG. 3 represents that the data collection program 220 causes the delivered AI model 26 according to the designated execution condition to execute the addition processing.

An operation [8] in FIG. 3 indicates that the delivered AI model 26 that has received the execution instruction in the operation [7] additionally generates the secondary data. An operation [9] in FIG. 3 indicates that the secondary data (result data) generated by the delivered AI model 26 is stored in an appropriate location.

In a case where the generation of the designated number of pieces of secondary data is finished, the delivered AI model 26 notifies the data collection program 220 that the additional generation processing ends. An operation [10] in FIG. 3 represents an operation of notifying the data collection program 220 that the addition processing for the designated number of pieces of data ends.

The data collection program 220 that has received this notification notifies the local learning management program 250 that the necessary learning data has been prepared in an operation [11] to cause the local learning management program 250 to start the training of the local model to be trained LM. A flow of subsequent operations related to learning is the same repetition as the flow of the operations [8] to [11] described with reference to FIG. 1. Operations [12], [13], and [14] in FIG. 3 are the same as the operations [9], [10], and [11] in FIG. 1.

[Case of Assumption C]

In a case where the learning data for the model to be trained that uses only the secondary data as the learning data is insufficient as in the assumption C, the secondary data is additionally generated in the same flow as the operations [5] to [14] described in the case of the assumption B, and the learning proceeds.

<<System Configuration Example>>

Figure 4:
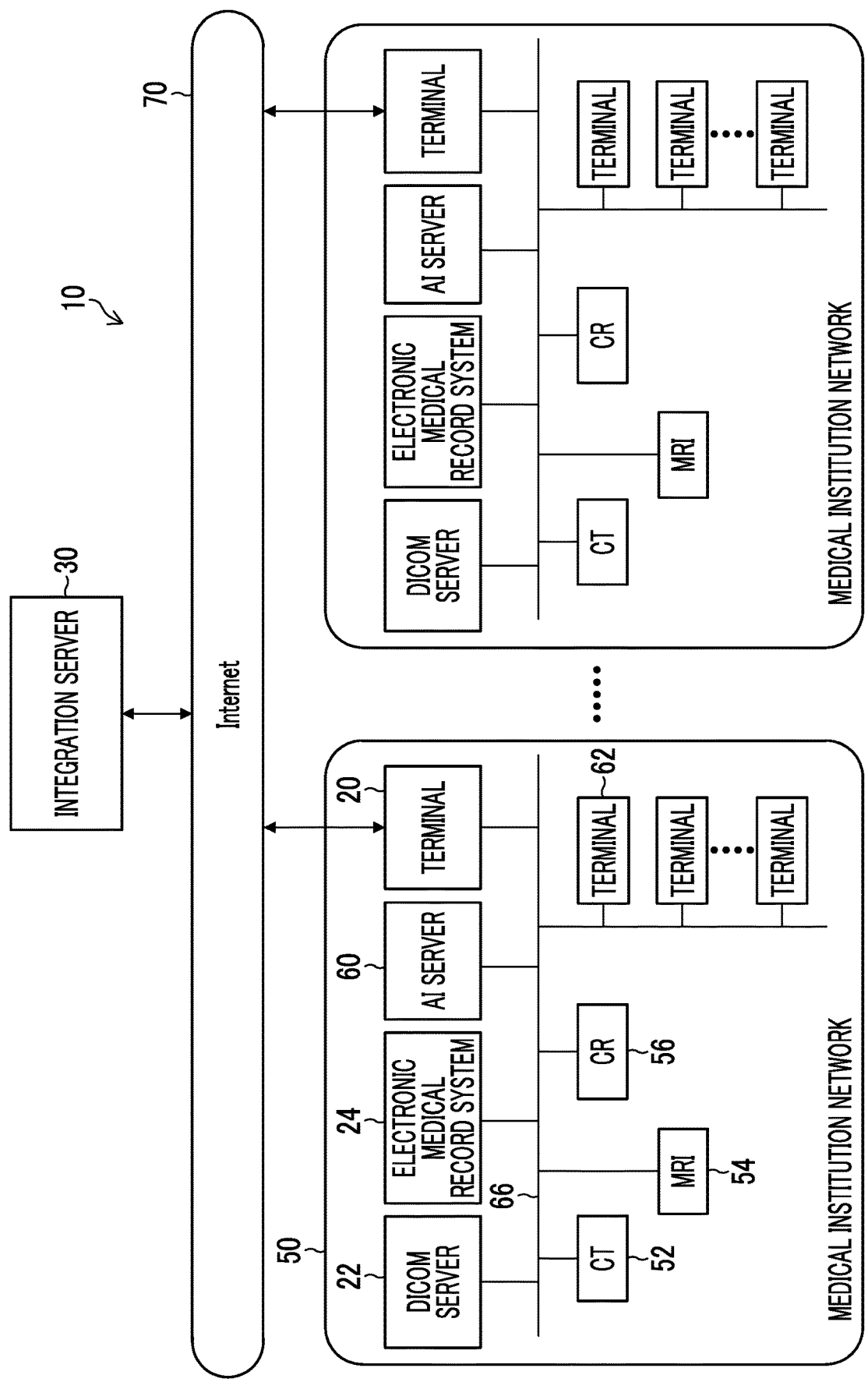
FIG. 4 is a diagram schematically showing a system configuration example of the machine learning system according to the embodiment of the present invention.

Next, an example of a specific configuration of the machine learning system 10 will be described. FIG. 4 is a diagram schematically showing a system configuration example of the machine learning system 10. First, an example of a medical institution network 50 will be described. For simplicity of illustration, FIG. 4 shows an example in which the medical institution network 50 having an identical system configuration is installed in each of a plurality of medical institutions. However, a medical institution network having a different system configuration for each medical institution may be constructed.

The medical institution network 50 is a computer network including a CT apparatus 52, an MRI apparatus 54, a computed radiography (CR) apparatus 56, a DICOM server 22, an electronic medical record system 24, an AI server 60, terminals 20 and 62, and an internal communication line 66.

The medical institution network 50 is not limited to the CT apparatus 52, the MM apparatus 54, and the CR apparatus 56 illustrated in FIG. 4. Instead of some or all of the apparatuses or in addition to the apparatuses, the medical institution network 50 may include at least one or a combination of a digital X-ray imaging apparatus, an angiography X-ray diagnosis apparatus, an ultrasound diagnostic apparatus, a positron emission tomography (PET) apparatus, an endoscopic apparatus, a mammography apparatus, and various inspection apparatuses (modalities) which are not illustrated. There may be various combinations of types of inspection apparatuses connected to the medical institution network 50 for each medical institution.

The DICOM server 22 performs a communication with another apparatus via the internal communication line 66, and transmits and receives various pieces of data including image data. The DICOM server 22 receives various pieces of data including image data and the like generated by each inspection apparatus such as the CT apparatus 52, the Mill apparatus 54, and the CR apparatus 56 through the internal communication line 66, and stores and manages the data in a recording medium such as a large-capacity external storage device.

A storage format of the image data and the communication between the apparatuses through the internal communication line 66 are based on a protocol such as DICOM. Various pieces of data stored on the medical institution network 50 such as the DICOM server 22 and the electronic medical record system 24 can be used as learning data. The learning data created based on the data stored in the DICOM server 22 and/or in the electronic medical record system 24 and the like can be stored in the terminal 20 or in another appropriate storage.

The AI server 60 executes CAD processing using an AI model already provided as a commercial version. The AI server 60 includes at least one AI processing module, such as lung CAD and/or brain CAD. The AI processing module in the AI server 60 corresponds to the delivered AI model 26 described with reference to FIG. 3. The AI processing module in the AI server 60 and the delivered AI model 26 are examples of "third program" in the present disclosure. The AI server 60 may include a plurality of types of delivered AI models 26.

The AI server 60 can acquire the data from the DICOM server 22 and the like via the internal communication line 66. The various pieces of data stored in databases of the DICOM server 22 and/or the electronic medical record system 24 and the like and various pieces of information including the inference result by the AI server 60 can be displayed on the terminals 20 and 62 connected to the internal communication line 66.

As described with reference to FIG. 1, the terminal 20 is a training processing terminal that executes the local learning. The terminal 20 has a communication function for communicating with the integration server 30 and is connected to the integration server 30 via a wide area communication line 70. The terminal 20 can acquire the data from the DICOM server 22 and/or from the electronic medical record system 24 and the like via the internal communication line 66. Further, the terminal 20 has authority to execute the AI processing module in the AI server 60 and causes the AI processing module to operate for the additional generation of new learning data in a case where an instruction indicating that the data is required to be additionally generated is received from the integration server 30. Some or all of processing functions of the terminal 20 may be loaded on the AI server 60.

On the other hand, a terminal 62 may be a display terminal referred to as a PACS viewer or a DICOM viewer. A plurality of terminals 62 may be connected to the medical institution network 50. A form of the terminals 20 and 62 is not particularly limited and may be a personal computer, a workstation, a tablet terminal, or the like.

As shown in FIG. 4, the medical institution network 50 having the same system configuration is constructed in each of the plurality of medical institutions. The integration server 30 communicates with the terminal 20 of each medical institution network via the wide area communication line 70. The wide area communication line 70 is an example of "communication line" according to the present disclosure.

<<Configuration Example of Integration Server 30>>

Figure 5:
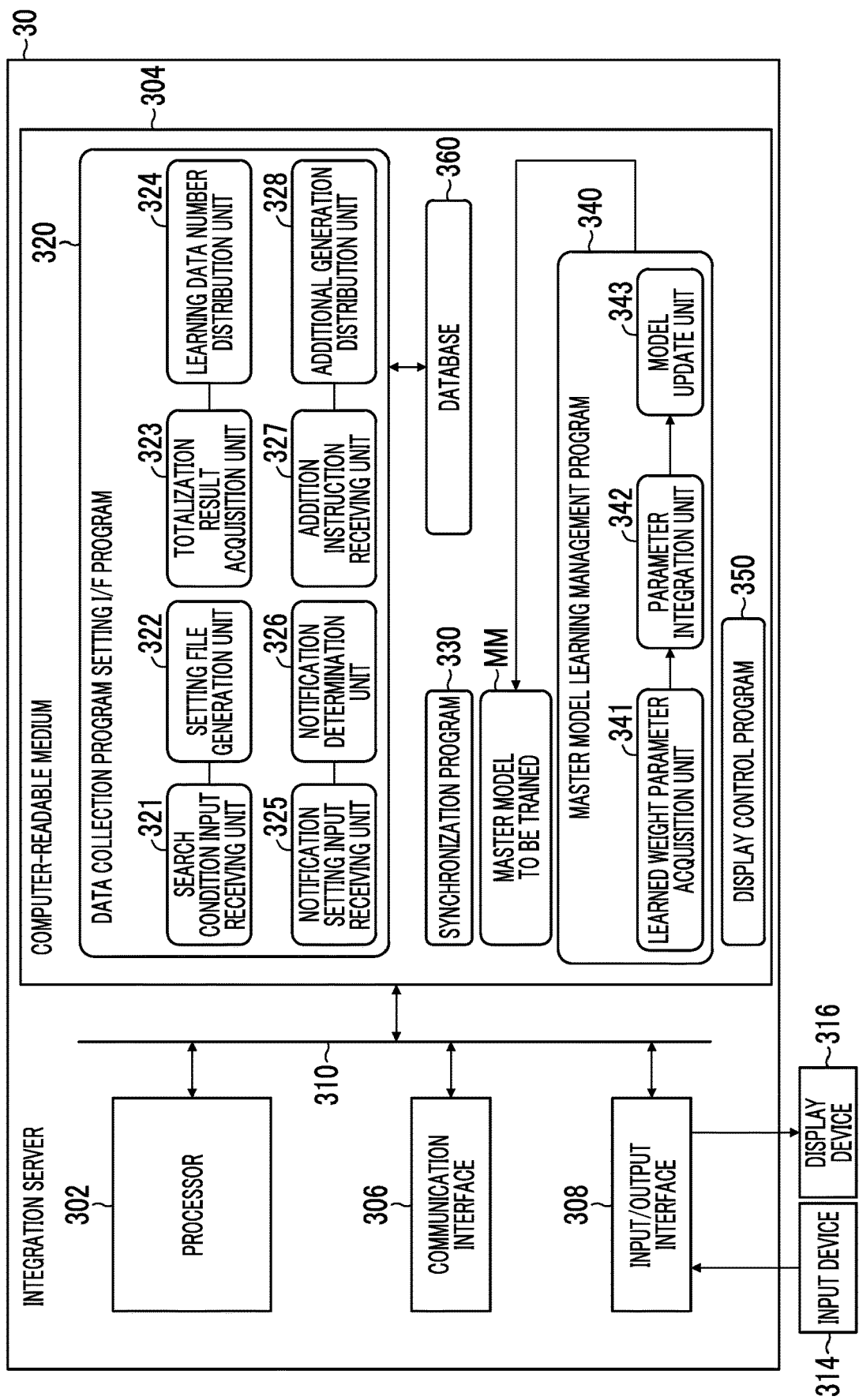
FIG. 5 is a block diagram showing a configuration example of an integration server.

FIG. 5 is a block diagram showing a configuration example of the integration server 30. The integration server 30 can be formed by a computer system configured by using one or a plurality of computers. The integration server 30 is formed by installing a program on a computer.

The integration server 30 comprises a processor 302, a non-transitory tangible computer-readable medium 304, a communication interface 306, an input/output interface 308, a bus 310, an input device 314, and a display device 316. The processor 302 is an example of "second processor" according to the present disclosure. The computer-readable medium 304 is an example of "second computer-readable medium" according to the present disclosure.

The processor 302 includes a central processing unit (CPU). The processor 302 may include a graphics processing unit (GPU). The processor 302 is connected to the computer-readable medium 304, the communication interface 306, and the input/output interface 308 via the bus 310. The input device 314 and the display device 316 are connected to the bus 310 via the input/output interface 308.

The computer-readable medium 304 includes a memory as a main memory and a storage as an auxiliary storage device. The computer-readable medium 304 may be, for example, a semiconductor memory, a hard disk drive (HDD) device, a solid state drive (SSD) device, or a combination of these devices.

The integration server 30 is connected to the wide area communication line 70 (refer to FIG. 4) via the communication interface 306.

The computer-readable medium 304 stores various programs and pieces of data including a data collection program setting I/F program 320, a synchronization program 330, a master model to be trained MM, a master model learning management program 340, a display control program 350, and a database 360.

The data collection program setting I/F program 320 is a program for realizing the data collection program setting interface 32 described with reference to FIGS. 1 and 3. In a case where the processor 302 executes a command of the data collection program setting I/F program 320, a computer is caused to function as the data collection program setting interface 32 (refer to FIG. 1), together with user interfaces including the input device 314 and the display device 316.

By executing the command of the data collection program setting I/F program 320, the processor 302 functions as a search condition input receiving unit 321, a setting file generation unit 322, a totalization result acquisition unit 323, and a learning data number distribution unit 324. The search condition input receiving unit 321 receives the input of the search condition from an operator of the development entity 80. The setting file generation unit 322 generates the search condition setting file based on the input search condition. The totalization result acquisition unit 323 acquires, from the terminal 20 of each medical institution, the totalization result of the number of pieces of data that matches the search condition and stores the totalization result in the database 360.

The learning data number distribution unit 324 distributes the number of pieces of learning data used for learning at each medical institution according to a predetermined distribution rule based on the totalization result obtained from the terminal 20 of each medical institution and transmits the distribution information to the data collection program 220 of each medical institution.

The processor 302 executes the command of the data collection program setting I/F program 320 to function as a notification setting input receiving unit 325, a notification determination unit 326, an addition instruction receiving unit 327, and an additional generation distribution unit 328. The notification setting input receiving unit 325 receives an input related to the notification setting described as [Case of Assumption A]. The notification determination unit 326 determines whether or not the total number of pieces of the data that matches the search condition is equal to or larger than the required number to determine whether or not the notification is possible. As described as [Case of Assumption B] and [Case of Assumption C], the addition instruction receiving unit 327 receives an input for designating the type and number of pieces of data to be added. The additional generation distribution unit 328 distributes the additional generation processing to each medical institution based on the designated type and on the number of pieces of additional data. The additional generation distribution unit 328 generates additional generation distribution information including designation of the number of pieces of additional data in a case where each terminal 20 is requested to additionally generate data and transmits this additional generation distribution information to each terminal 20.

The synchronization program 330 is a program for providing the data of the master model to be trained MM to the terminal 20 of each medical institution via the communication interface 306 and synchronizing the local model LM of each terminal 20 with the master model MM. The processor 302 executes a command of the synchronization program 330 to cause the computer to function as a synchronization processing unit. The synchronization program 330 may be incorporated as a program module of the master model learning management program 340.

The master model learning management program 340 integrates the learned weight parameters as the learning results of the local learning performed in the terminals 20 in the plurality of medical institutions to perform processing of updating the weight parameter of the master model to be trained MM. The processor 302 executes a command of the master model learning management program 340 to cause the computer to function as a learned weight parameter acquisition unit 341, a parameter integration unit 342, and a model update unit 343. The learned weight parameter acquisition unit 341 acquires the learned weight parameter as the learning result of the local learning performed in the terminals 20 in the plurality of medical institutions.

The parameter integration unit 342 integrates the learned weight parameters obtained from the plurality of medical institutions. The integration processing may be processing of obtaining a simple average value or processing of obtaining a weighted average value with appropriate weighting. The model update unit 343 updates the parameter of the master model to be trained MM by an integration parameter calculated by the parameter integration unit 342.

Although not shown in FIG. 3, the computer-readable medium 304 of the integration server 30 may store an accuracy verification program for verifying the inference accuracy of the master model to be trained MM and data for verification. For example, the inference accuracy is checked for a master model candidate including the parameter integrated by the parameter integration unit 342, and the model update unit 343 may update the master model MM in a case where a model with inference accuracy exceeding an accuracy target value is obtained. The accuracy target value is a value indicating a target inference accuracy. For example, the inference accuracy is set higher than the inference accuracy of the latest version of the master model MM, and the master model MM and the accuracy target value are updated every time the inference accuracy is improved. Alternatively, for example, the accuracy target value may be set to a level of accuracy that can be commercialized in place of the master model MM.

The data collection program setting I/F program 320 and the master model learning management program 340 are examples of "second program" in the present disclosure.

Further, in a case where the processor 302 executes a command of the display control program 350, the computer is caused to function as a display control unit. The display control unit generates a signal for display required for a display output to the display device 316 and performs display control of the display device 316.

The display device 316 is configured with, for example, a liquid crystal display, an organic electro-luminescence (OEL) display, a projector, or an appropriate combination thereof. The input device 314 is configured with, for example, a keyboard, a mouse, a touch panel, another pointing device, a voice input device, or an appropriate combination thereof. The input device 314 receives various inputs from an operator. The display device 316 and the input device 314 may be integrally configured by using a touch panel.

The display device 316 can display the inference accuracy in each learning iteration of each master model to be trained MM. The operator can check the progress of training of the master model to be trained MM via the information displayed on the display device 316.

<<Example of Data Collection Program Setting I/F Program 320>>

Figure 6:
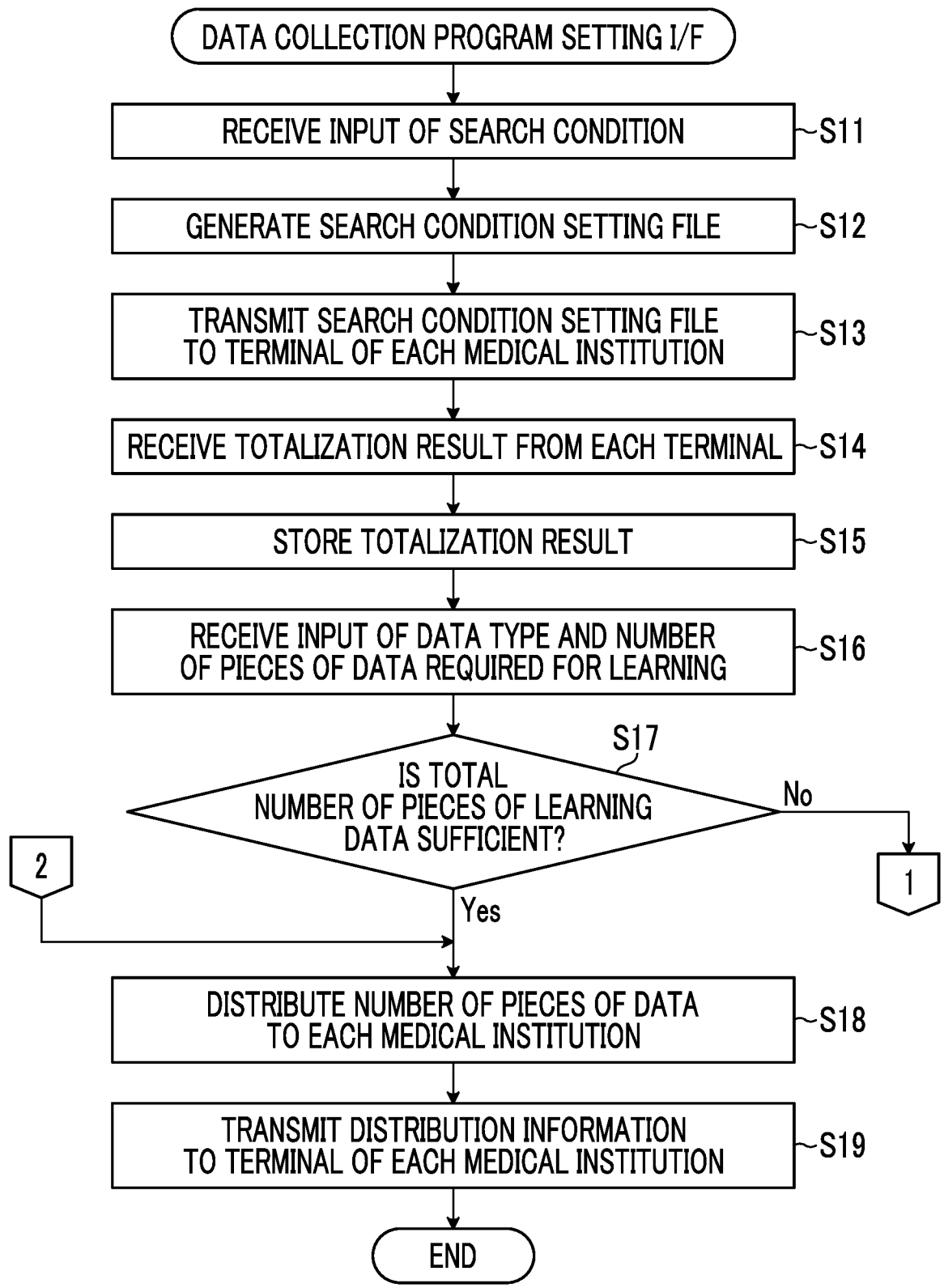
FIG. 6 is a flowchart showing an example of an operation of the integration server based on a data collection program setting I/F program.

FIG. 6 is a flowchart showing an example of the operation of the integration server 30 based on the data collection program setting I/F program 320. Steps in the flowchart shown in FIG. 6 are executed by the processor 302 of the integration server 30 according to the command of the data collection program setting I/F program 320.

In step S11, the processor 302 receives the input of the search condition. The operator of the development entity 80 can input information designating the search condition from the input device 314.

In step S12, the processor 302 generates the search condition setting file according to the information input in step S11.

In step S13, the processor 302 transmits the search condition setting file to the terminal 20 of each medical institution.

In step S14, the processor 302 receives, from each terminal 20, the totalization result of the number of pieces of data that matches the search condition. A time of acquiring the totalization result from each terminal 20 may be an appropriate time for each terminal 20.

In step S15, the processor 302 stores the totalization result from each terminal 20 in the database 360 or the like. The processor 302 can display the totalization result from each terminal 20 on the display device 316.

In step S16, the processor 302 receives the input of the data type and the number of pieces of data required for learning. In a case where the data type required for learning is the same as the data type designated in the search condition, input contents of the search condition may be used. The operator of the development entity 80 can input information designating the data type and the number of pieces of data required for learning from the input device 314.

In step S17, the processor 302 determines whether or not the total number of pieces of learning data is sufficient for the required number. In a case where the determination result in step S17 is a Yes determination, that is, in a case where the total number of pieces of learning data is equal to or larger than the required number, the processor 302 proceeds to step S18.

In step S18, the processor 302 distributes the number of pieces of data to each medical institution. Then, in step S19, the processor 302 transmits the distribution information including the number of pieces of learning data for each medical institution distributed in step S18 to the terminal 20 of each medical institution.

Figure 7:
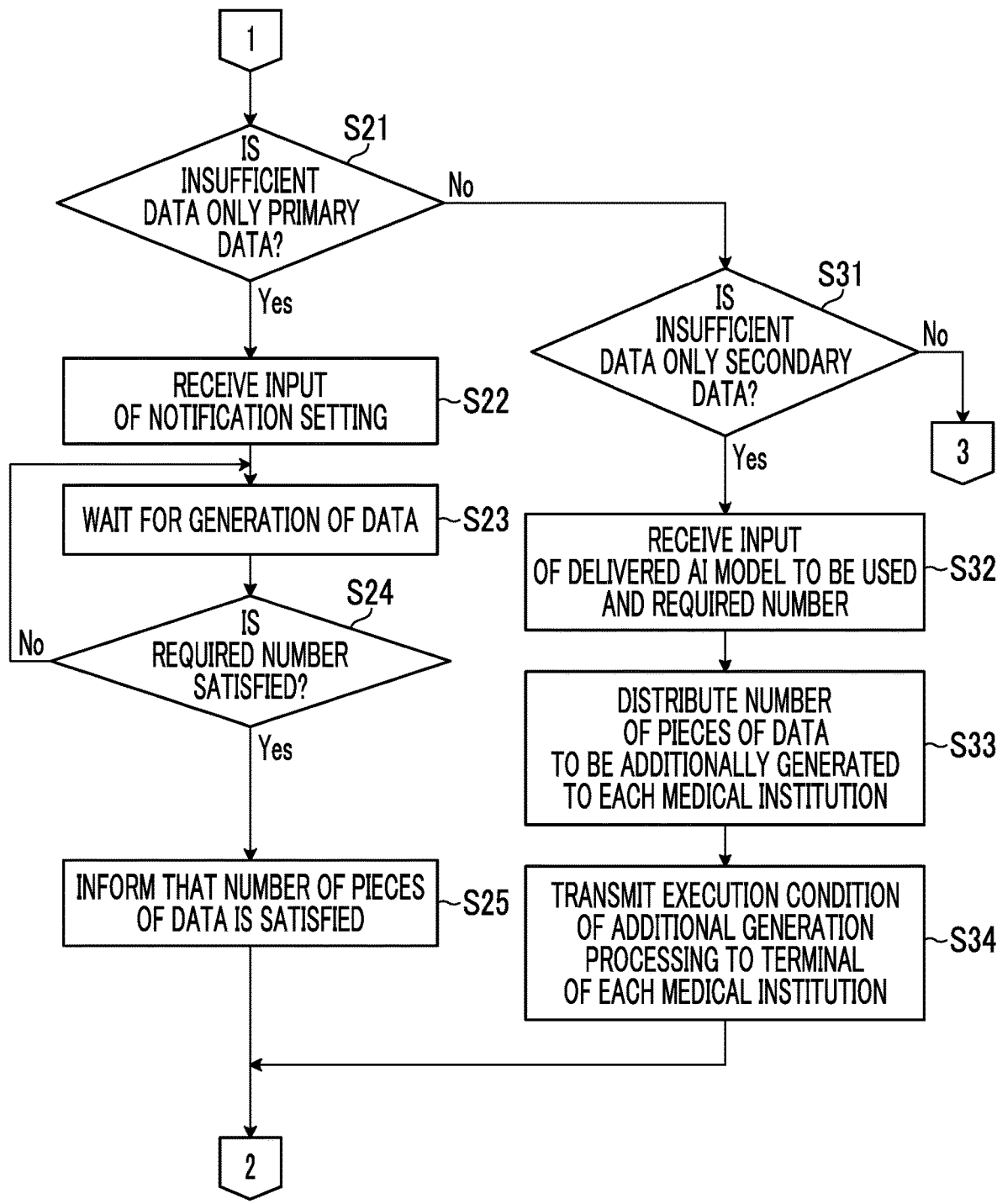
FIG. 7 is a flowchart showing the example of the operation of the integration server based on the data collection program setting I/F program.

On the other hand, in a case where the determination result in step S17 is a No determination, that is, in a case where the total number of pieces of learning data is less than the required number, the processor 302 proceeds to step S21 in FIG. 7.

In step S21, the processor 302 determines whether or not the insufficient data is only the primary data. This determination processing is a step of determining whether or not the case is such as [Case of Assumption A].

In a case where the determination result in step S21 is a Yes determination, the processor 302 proceeds to step S22.

In step S22, the processor 302 receives an input of a notification setting in a case where the notification is made at the stage where the required number of pieces of primary data is prepared.

In step S23, the processor 302 waits for the necessary data to be newly generated. The processor 302 receives information on the latest totalization result from the terminal 20 of each medical institution at an appropriate time. With the generation of new primary data in the medical institution system MS, the information on the totalization result is updated.

In step S24, the processor 302 determines whether or not the number of pieces of insufficient primary data satisfies the required number. In a case where the determination result in step S24 is a No determination, that is, in a case where the primary data is insufficient, the processor 302 returns to step S23.

In a case where the determination result in step S24 is a Yes determination, that is, in a case where the required number of pieces of primary data or more are prepared, the processing proceeds to step S25.

In step S25, the processor 302 makes a notification informing that the number of pieces of data required for learning is satisfied. The development entity 80 can receive this notification through the display device 316.

On the other hand, in a case where the determination result in step S21 is a No determination, the processor 302 proceeds to step S31. In step S31, the processor 302 determines whether or not the insufficient data is only the secondary data. This determination processing is a step of determining whether or not the case is such as [Case of Assumption B] or [Case of Assumption C]. Meanwhile, in a case where the determination result in step S23 is a Yes determination, the processor 302 proceeds to step S32.

In step S32, the processor 302 receives the input of the delivered AI model to be used and the required number of pieces of data to be added in order to additionally generate new secondary data. The operator of the development entity 80 can input information such as a required data type and the number of pieces of additional data from the input device 314.

In step S33, the processor 302 distributes the number of pieces of data to be additionally generated to each medical institution based on the information designated in step S32.

In step S34, the processor 302 transmits the execution condition of the additional generation processing distributed to each medical institution to the terminal 20 of each medical institution.

After step S34 or step S25, the processor 302 proceeds to step S18 in FIG. 6.

Figure 8:
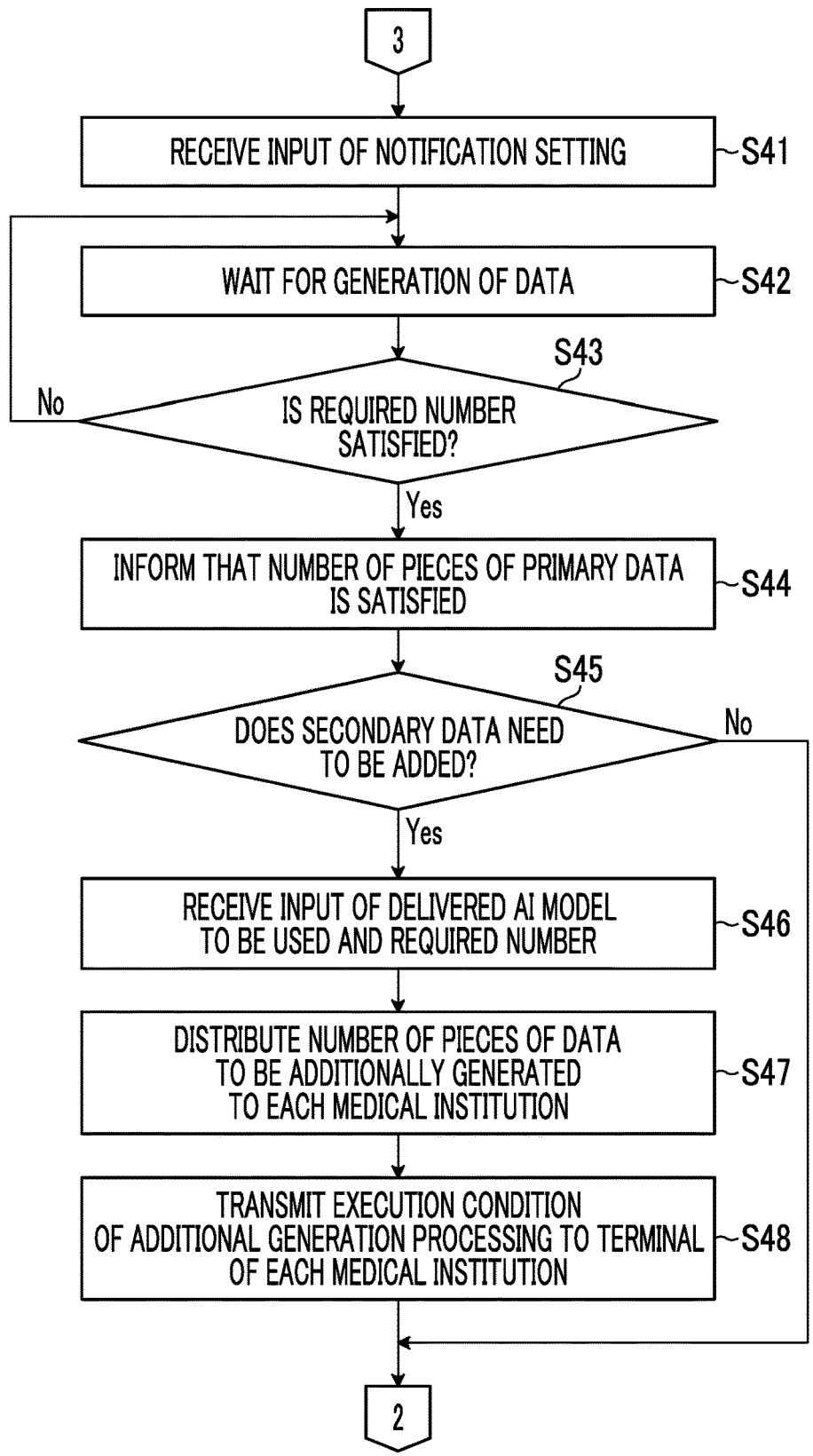
FIG. 8 is a flowchart showing the example of the operation of the integration server based on the data collection program setting I/F program.

Further, in a case where the determination result in step S31 of FIG. 7 is a No determination, that is, in a case where both types of primary data and secondary data are insufficient, the processor 302 proceeds to step S41 of FIG. 8. Steps S41 to S44 are the same as the corresponding steps of steps S22 to S25 of FIG. 7. After step S44, in step S45, the processor 302 determines whether or not the secondary data needs to be added.

During a period in a case where new primary data is generated, new secondary data may also be generated. In a case where the determination result in step S45 is a Yes determination, the processor 302 proceeds to step S46. Steps S46 to S48 are the same as the corresponding steps of steps S32 to S34 in FIG. 7. After step S48, the processor 302 proceeds to step S18 of FIG. 6.

On the other hand, in a case where the determination result of step S45 in FIG. 8 is a No determination, steps S46 to S48 are skipped, and the processing proceeds to step S18 in FIG. 6.

The processor 302 ends the flowchart of FIG. 6 after step S19.

<<Configuration Example of Terminal 20 on Medical Institution Network 50>>

Figure 9:
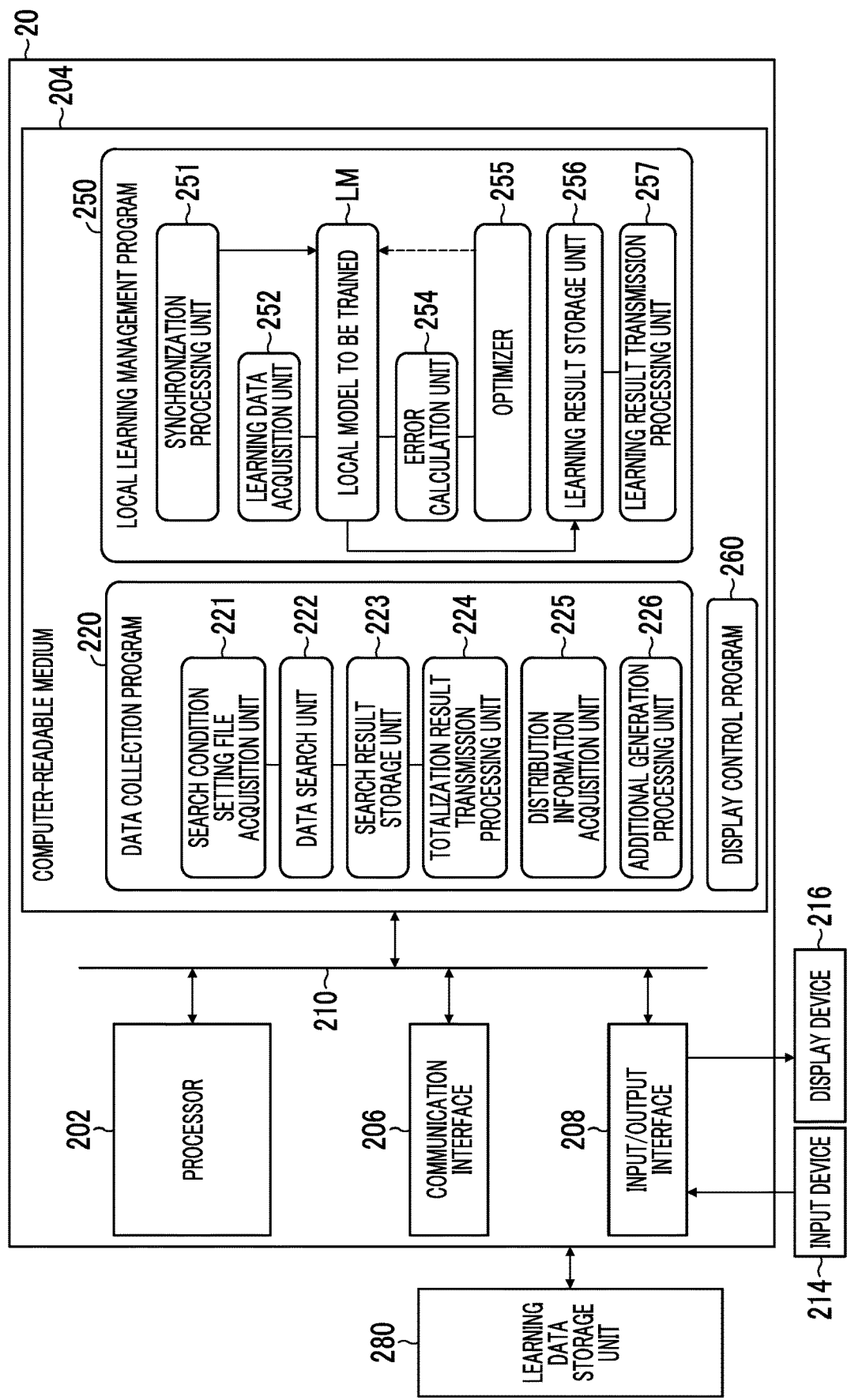
FIG. 9 is a block diagram showing a configuration example of a terminal on a medical institution network.

FIG. 9 is a block diagram showing a configuration example of the terminal 20 on the medical institution network 50. The terminal 20 performing the local learning can be formed by a computer system configured by using one or a plurality of computers.

The terminal 20 comprises a processor 202, a non-transitory tangible computer-readable medium 204, a communication interface 206, an input/output interface 208, a bus 210, an input device 214, and a display device 216. A hardware configuration of the terminal 20 may be the same as the hardware configuration of the integration server 30 described with reference to FIG. 5. That is, the hardware configurations of the processor 202, the computer-readable medium 204, the communication interface 206, the input/output interface 208, the bus 210, the input device 214, and the display device 216 shown in FIG. 9 may be the same as the corresponding elements shown in FIG. 5.

The terminal 20 is an example of "information processing apparatus" according to the present disclosure. The processor 202 is an example of "first processor" according to the present disclosure. The computer-readable medium 204 is an example of "first computer-readable medium" according to the present disclosure.

The terminal 20 is connected to a learning data storage unit 280 via the communication interface 206 or via the input/output interface 208. The learning data storage unit 280 is configured to include a storage that stores the learning data to be used for machine learning by the terminal 20. The term "learning data" is data for training used for machine learning and is synonymous with "data for learning" or "training data". The learning data storage unit 280 may be a storage or the like of the DICOM server 22 and/or of the electronic medical record system 24 described with reference to FIG. 3 and may be a storage corresponding to "appropriate location" described as the operation [9] of FIG. 3.

Here, an example in which the learning data storage unit 280 and the terminal 20 that executes the training processing are configured as separate apparatuses will be described. However, the functions may be formed by one computer, or the processing functions may be shared and formed by two or more computers.

The computer-readable medium 204 of the terminal 20 shown in FIG. 9 stores various programs, which include the data collection program 220 and the local learning management program 250, and data. The data collection program 220 and the local learning management program 250 are examples of "first program" in the present disclosure.

The processor 202 executes a command of the data collection program 220 to cause the computer to function as a search condition setting file acquisition unit 221, a data search unit 222, a search result storage unit 223, a totalization result transmission processing unit 224, a distribution information acquisition unit 225, and an additional generation processing unit 226. The search condition setting file acquisition unit 221 acquires the search condition setting file from the integration server 30.

The data search unit 222 searches for the data that matches the search condition from a database or the like on the medical institution network 50 based on the search condition described in the search condition setting file. The search result by the data search unit 222 is stored in the search result storage unit 223. The totalization result transmission processing unit 224 performs processing of totaling the search results stored in the search result storage unit 223 and transmitting information on the number of pieces of data that matches the search condition (totalization result) to the integration server 30.

The distribution information acquisition unit 225 acquires, from the integration server 30, the distribution information including the designation of the number of pieces of data to be used for learning. The data collection program 220 causes the local learning management program 250 to perform the local learning using the learning data of the number of pieces of data designated in the distribution information.

In a case where the total number of pieces of data required for learning is less than the required number, the additional generation processing unit 226 causes the delivered AI model 26 to operate to additionally generate the number of pieces of additional data related to the designation in accordance with the instruction for the additional generation from the integration server 30.

The processor 202 executes a command of the local learning management program 250 to cause the computer to function as a synchronization processing unit 251, a learning data acquisition unit 252, the local model to be trained LM, an error calculation unit 254, an optimizer 255, a learning result storage unit 256, and a learning result transmission processing unit 257.

The synchronization processing unit 251 communicates with the integration server 30 via the communication interface 206 to synchronize the master model to be trained MM in the integration server 30 with the local model to be trained LM in the terminal 20 side.

The learning data acquisition unit 252 acquires the learning data that matches the search condition from the learning data storage unit 280. The number of pieces of learning data used for local learning is the number of pieces of data designated in the distribution information. The learning data acquisition unit 252 may be configured to include a data input terminal for receiving data from an external apparatus or from another signal processing unit in the apparatus. Further, the learning data acquisition unit 252 may be configured to include the communication interface 206, the input/output interface 208, a media interface for performing reading and writing on a portable external storage medium such as a memory card (not shown), or an appropriate combination of these interfaces.

The learning data acquired via the learning data acquisition unit 252 is input to the local model to be trained LM.

The error calculation unit 254 calculates an error between a predicted value indicated by a score which is output from the local model to be trained LM and the correct answer data. The error calculation unit 254 evaluates the error using a loss function. The loss function may be, for example, a cross entropy or a mean square error.

The optimizer 255 performs processing of updating a weight parameter of the local model to be trained LM from the calculation result of the error calculation unit 254. The optimizer 255 performs calculation processing of obtaining an update amount of the weight parameter of the local model to be trained LM and update processing of the weight parameter of the local model to be trained LM according to the calculated update amount of the weight parameter, by using the error calculation result obtained from the error calculation unit 254. The optimizer 255 updates the weight parameter based on an algorithm such as backpropagation.

The terminal 20 in which the local learning management program 250 is incorporated functions as a local learning apparatus that executes the machine learning on the terminal 20 by using the local data in the medical institution as learning data. The terminal 20 reads the learning data, which is the local data, from the learning data storage unit 280 to execute the machine learning for the local model to be trained LM using the learning data of the number of pieces of data designated in the distribution information. The terminal 20 can update, in a case where the learning data is read in units of mini-batch in which a plurality of pieces of learning data are collected, the weight parameter.

The local learning management program 250 repeats an iteration of the training processing until a learning end condition is satisfied for the local model to be trained LM. After the learning end condition is satisfied, the weight parameter of the local model to be trained LM is stored in the learning result storage unit 256 as the learning result.

The learning result transmission processing unit 257 performs processing of transmitting the learning result (that is, the learned weight parameter) to the integration server 30. The weight parameter of the trained local model to be trained LM stored in the learning result storage unit 256 is transmitted to the integration server 30 via the communication interface 206 through the wide area communication line 70 (refer to FIG. 4).

The processor 202 executes a command of a display control program 260 to cause the computer to function as the display control unit. The display control unit generates a signal for display required for a display output to the display device 216 and performs display control of the display device 216. Further, although not shown in FIG. 4, the computer-readable medium 204 of the terminal 20 may store an accuracy verification program for verifying the inference accuracy of the local model to be trained LM and data for verification.

As described above, the local learning management program 250 is constructed on the terminal 20 on the medical institution network 50. The local learning management program 250 has a function of synchronizing the master model MM before performing training with the local model LM, a function of starting the local learning, a function of setting an end condition of local learning, and a function of transmitting the result of local learning to the integration server 30 in a case where the local learning ends.

<<Example of Data Collection Program 220>>

Figure 10:
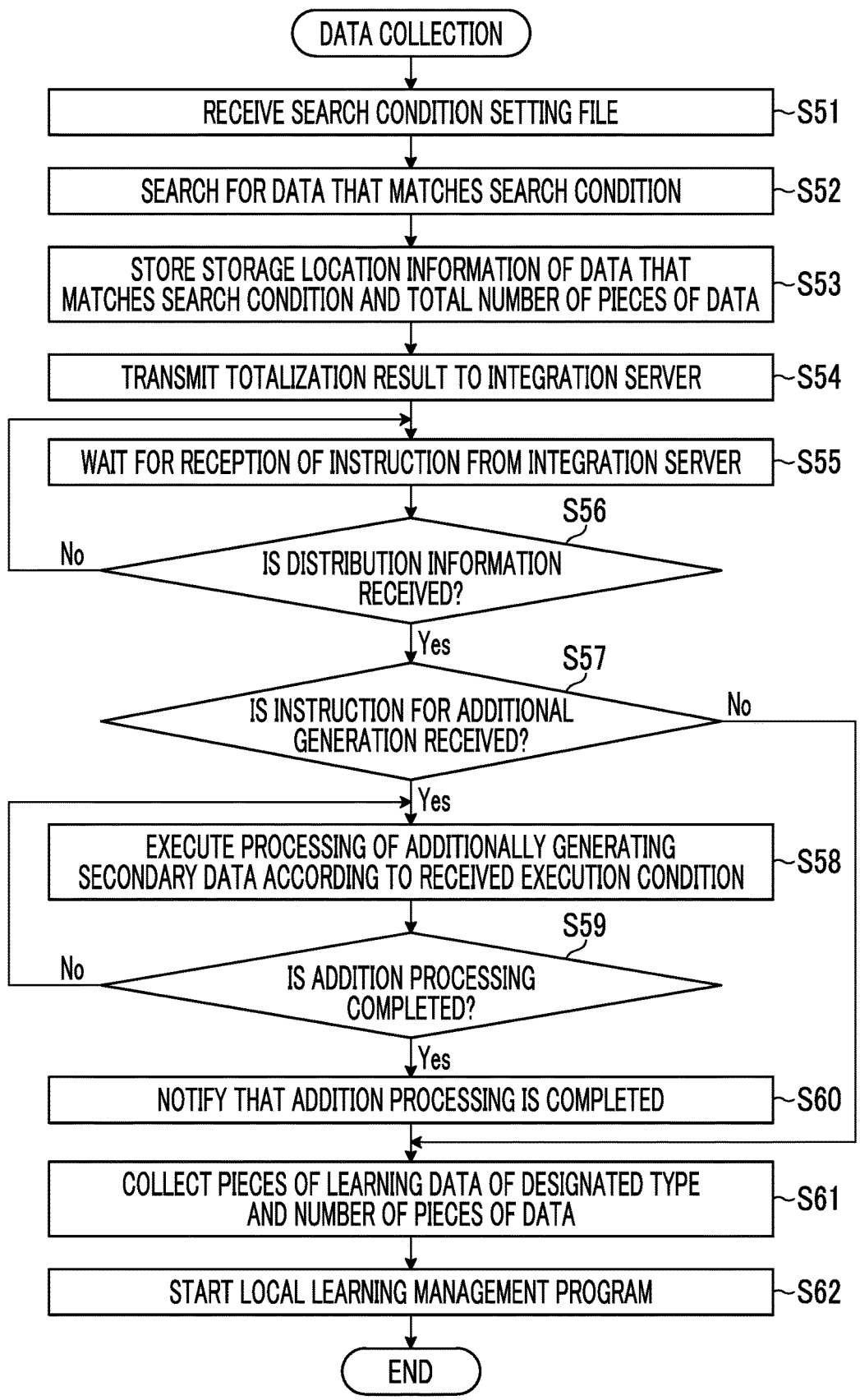
FIG. 10 is a flowchart showing an example of an operation of a terminal based on a data collection program.

FIG. 10 is a flowchart showing an example of the operation of the terminal 20 based on the data collection program 220. Steps in the flowchart shown in FIG. 10 are executed by the processor 202 according to the command of the data collection program 220.

In step S51, the processor 202 receives the search condition setting file from the integration server 30. The search condition setting file transmitted from the integration server 30 in step S13 of FIG. 6 is received by the processor 202.

Next, in step S52 of FIG. 10, the processor 202 searches for the data that matches the search condition set in the search condition setting file from within the medical institution system MS.

In step S53, the processor 202 stores the storage location information of the data that matches the search condition and totals the number of pieces of data.

In step S54, the processor 202 transmits the totalization result obtained in step S53 to the integration server 30.

Thereafter, in step S55, the processor 202 waits for the reception of the instruction from the integration server 30.

In step S56, the processor 202 determines whether or not the distribution information has been received from the integration server 30. In a case where the determination result in step S56 is a No determination, the processing returns to step S55. In a case where the determination result in step S56 is a Yes determination, that is, in a case where the processor 202 receives the distribution information, the processing proceeds to step S57.

In step S57, the processor 202 determines whether or not the instruction for the additional generation has been received. In a case where the determination result in step S57 is a No determination, that is, in a case where new learning data is not necessary to be added, the processor 202 proceeds to step S61.

In a case where the determination result in step S57 is a Yes determination, that is, in a case where new learning data is necessary to be added by the additional generation of the secondary data, the processor 202 proceeds to step S58.

In step S58, the processor 202 causes the delivered AI model 26 to execute processing of additionally generating the secondary data according to the received execution condition.

In step S59, the processor 202 determines whether or not the addition processing is completed. In a case where the determination result in step S59 is a No determination, the processing returns to step S58 and waits for the completion of the additional generation processing.

In a case where the determination result in step S59 is a Yes determination, that is, in a case where the generation of the secondary data of the number of pieces of additional data designated in the execution condition is completed, the processor 202 proceeds to step S60.

In step S60, the processor 202 notifies the local learning management program that the addition processing is completed.

Next, in step S61, the processor 202 collects the pieces of learning data of the type and number of pieces of data designated in the distribution information.

Then, in step S62, the processor 202 starts the local learning management program 250. After step S62, the processor 202 ends the flowchart of FIG. 10.

<<Example of Local Learning Management Program 250>>

Figure 11:
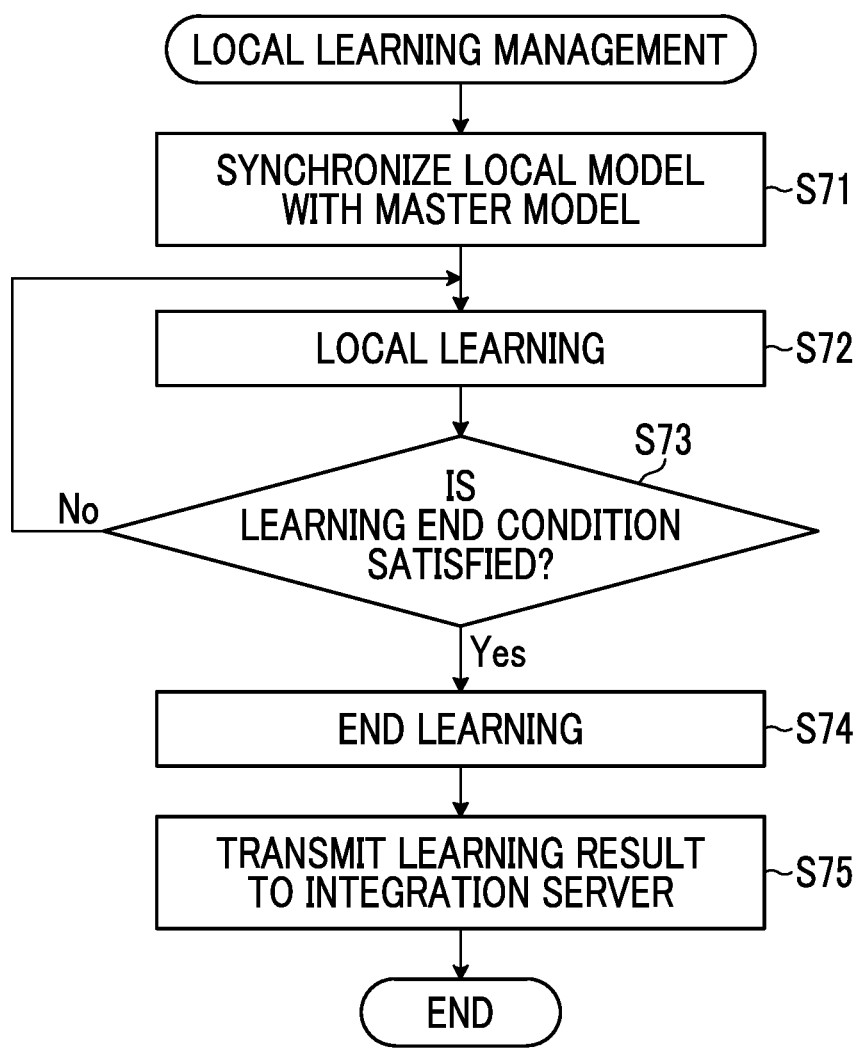
FIG. 11 is a flowchart showing the example of the operation of the terminal based on a local learning management program.

FIG. 11 is a flowchart showing an example of the operation of the terminal 20 based on the local learning management program 250. Steps in the flowchart shown in FIG. 11 are executed by the processor 202 according to the command of the local learning management program 250.

In step S71, the processor 202 synchronizes the local model LM with the master model MM. In a case where the local model LM is synchronized with the master model MM, for example, a form may be employed in which the parameter file used by the model is updated and the program reads the updated file to proceed with learning, or a form may be employed in which a virtual container image and the like are centrally managed in the integration server 30 side and are developed in the terminal 20 side. With the synchronization processing, the master model MM becomes the local model to be trained LM in an initial state before the learning is started.

In step S72, the processor 202 executes the local learning using the local data. The training processing on the local model LM synchronized with the master model MM is started by the local learning management program 250 to proceed with the local learning, using the local data in the medical institution system MS to which the terminal 20 belongs.

In step S73, the processor 202 determines whether or not the learning end condition is satisfied. Here, examples of the learning end condition include the following conditions.

[Example 1] The number of iterations is designated in advance, and learning is ended after the designated number of iterations.

[Example 2] The data for verification is stored in the medical institution network 50, and accuracy comparison is performed between the inference result obtained by inputting the data for verification into the trained model and the correct answer to calculate the inference accuracy. The learning is performed until the accuracy improvement of a designated ratio is achieved. That is, the inference accuracy of the learning model is calculated by using the data for verification, and the learning is ended in a case where the accuracy improvement of the designated ratio is achieved.

[Example 3] A time limit is set, and the learning is performed within the time limit. In a case where the time limit is reached, the learning is ended.

The end condition of any one of [Example 1] to [Example 3] may be set, or a logical product (AND) or a logical sum (OR) of the plurality of conditions may be set as the end condition.

In a case where the determination result in step S73 is a No determination, the processor 202 returns to step S72 to continue the local learning processing. On the other hand, in a case where the determination result in step S73 is a Yes determination, the processor 202 proceeds to step S74 to end the learning.

After the learning is ended, in step S75, the processor 202 transmits the learning result to the integration server 30. For example, the processor 202 stores the weight parameter of the trained model in a file and transmits the weight parameter thereof to the integration server 30 through the wide area communication line 70.

Each terminal 20 of the plurality of medical institutions executes the machine learning for each local model LM using the data on different medical institution networks 50 as learning data and transmits a learning result to the integration server 30 through the wide area communication line 70.

<<Example of Master Model Learning Management Program 340>>

Figure 12:
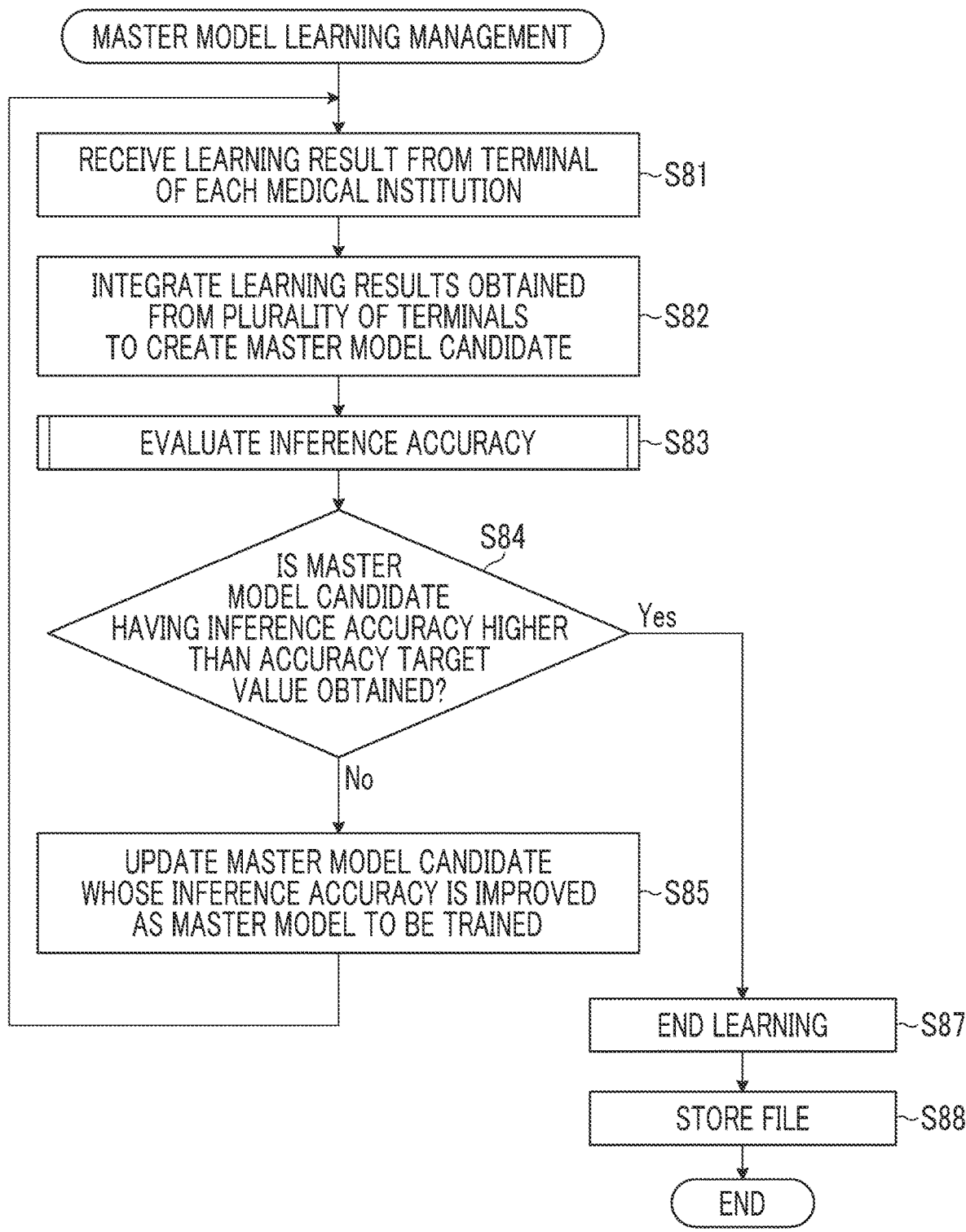
FIG. 12 is a flowchart showing the example of the operation of the integration server based on a master model learning management program.

FIG. 12 is a flowchart showing an example of an operation of the integration server 30 based on the master model learning management program 340. Steps in the flowchart shown in FIG. 12 are executed by the processor 302 of the integration server 30 according to the command of the master model learning management program 340.

In step S81, the processor 302 receives the learning result from the terminal 20 of each medical institution.

In step S82, the processor 302 integrates the learning results obtained from the plurality of terminals 20 to create the master model candidate.

In step S83, the processor 302 evaluates the inference accuracy for the created master model candidate. That is, the processor 302 causes the master model candidate to perform the inference by using the data for verification prepared in advance as an input to calculate the inference accuracy and compares the inference accuracy with the accuracy target value. Further, the processor 302 stores, in the database 360, the calculated inference accuracy and the comparison result between the inference accuracy and the accuracy target value in association (correlation) with the master model candidate.

For the inference accuracy of the master model candidate to be compared with the accuracy target value in a case where processing of step S83 is performed, an instantaneous value or a statistical value, such as an average value or a median value, is used as an appropriate value. An example of processing contents in the inference accuracy evaluation applied to step S83 will be described below with reference to FIG. 13.

In step S84, the processor 302 determines whether or not the master model candidate having an inference accuracy higher than the accuracy target value is obtained. In a case where the determination result in step S84 is a Yes determination, that is, in a case where the inference accuracy of the master model candidate exceeds the accuracy target value, the processor 302 ends the learning (step S87) and proceeds to step S88.

In step S88, the processor 302 sets a master model candidate having the inference accuracy higher than the accuracy target value, as the latest model having improved performance after learning, stores the model in the data storage unit such as the database 360 in an appropriate format such as a file, and sends notification that learning is ended. Here, as a notification method, a message queue, a general inter-processing communication, or the like may be used. The notification that the learning is ended may be displayed on the display device 316 or may be transmitted to the terminal 20. After step S88, the processor 302 ends the flowchart of FIG. 12.

On the other hand, in a case where the determination result in step S84 is a No determination, that is, in a case where the master model candidate having the inference accuracy higher than the accuracy target value is not obtained, the processor 302 proceeds to step S85.

In step S85, the processor 302 updates the master model candidate whose inference accuracy is improved as compared with the current master model MM as the master model to be trained MINI and next time, synchronizes this model with the local model LM of each terminal 20 and repeats steps S71 to S75 in FIG. 11 and steps S81 to S85 in FIG. 12. Accordingly, the local model LM with improved inference accuracy as compared with the inference accuracy before the update can be obtained.

<<Example of Inference Accuracy Evaluation Processing>>

Figure 13:
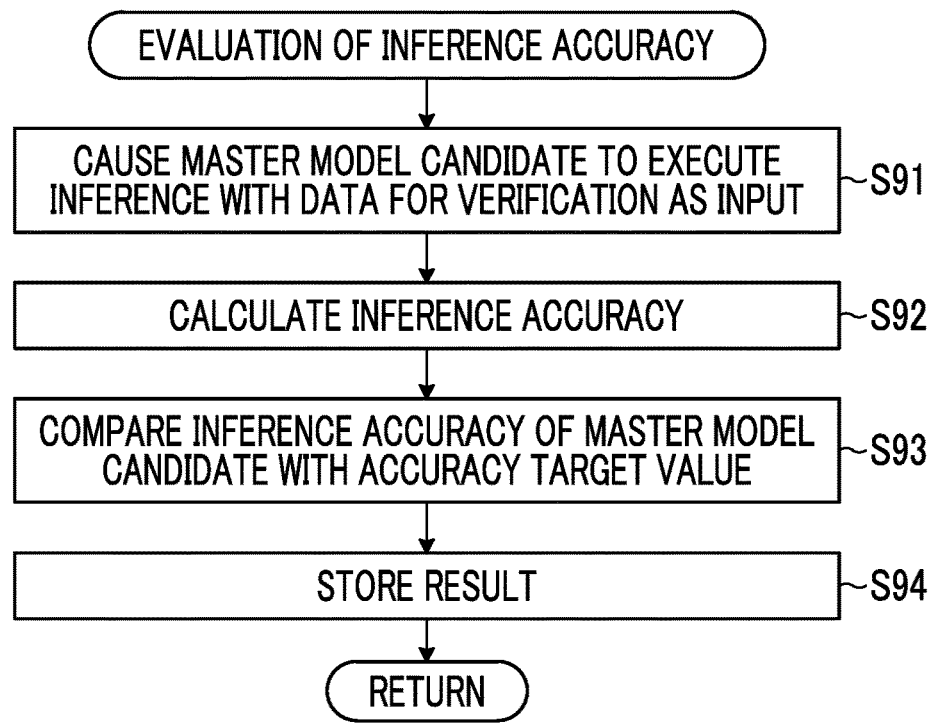
FIG. 13 is a flowchart showing an example of processing of evaluating an inference accuracy of a master model candidate in the integration server.

FIG. 13 is a flowchart showing an example of processing of evaluating the inference accuracy of the master model candidate in the integration server 30. The flowchart shown in FIG. 13 is applied to step S83 of FIG. 12.

In step S91 of FIG. 13, the processor 302 causes the master model candidate to execute the inference with the data for verification as an input.

In step S92, the processor 302 calculates the inference accuracy of the master model candidate based on the inference result and on the correct answer data.

In step S93, the processor 302 compares the inference accuracy of the master model candidate with the accuracy target value. The accuracy target value may be compared with an instantaneous value of the inference accuracy of the master model candidate. In the comparison, several iterations of the procedures of steps S81 to S93 may be performed, the inference accuracy at each iteration may be recorded each time, and a statistical value, such as an average value or a median value, of the recorded inference accuracies may be compared with the accuracy target value.

In step S94, the processor 302 stores the inference accuracy of the master model candidate and the comparison result between the inference accuracy and the accuracy target value in the database 360.

After step S94, the processor 302 ends the flowchart of FIG. 13 and returns to the flowchart of FIG. 12.

The integration server 30 performs the learning iteration until the master model MINI having the inference accuracy higher than the accuracy target value is obtained. Alternatively, in a case where the master model MINI having an inference accuracy higher than the accuracy target value is not obtained even though iterations are performed by the designated upper limit number of iterations, the integration server 30 may adopt the master model MM from which the maximum inference accuracy is obtained in the search processing so far, as the product model.

In the new master model MINI created by performing the machine learning method using the machine learning system 10 according to the present embodiment in this manner, the inference accuracy is improved as compared with the master model before the learning.

According to the present embodiment, it is possible to update an inference performance of the master model MM. In a case where the new master model created by performing the machine learning method according to the present embodiment is provided for sale or the like, preferably, the number of the clients used for the learning, the number of pieces of data for verification used for verification of the accuracy, and the like are described in an attached document provided at the time of sale. For the number of the clients used for the learning, for example, the classification of the clients is preferably displayed such as "hospital_how many cases", "clinic with bed_how many cases", and "clinic without bed_how many cases" as a client profile.

It is also conceivable to train the delivered AI model, which is the current product, as the master model to be trained MINI to upgrade the version from the delivered AI model. As a preliminary procedure in this case, information indicating the inference accuracy in the previous version and the inference accuracy in the new version and information indicating the number of the clients used for additional learning and the classification of the clients are presented to a medical institution, and an approval is received from the medical institution before the version is upgraded. After the approval is obtained, the version is upgraded.

The machine learning method implemented by the machine learning system 10 according to the present embodiment is an example of "inference model creation method" in the present disclosure, and the master model MINI after learning, which is obtained by learning, is an example of "inference model" in the present disclosure.

<<Example of Hardware Configuration of Computer>>

Figure 14:
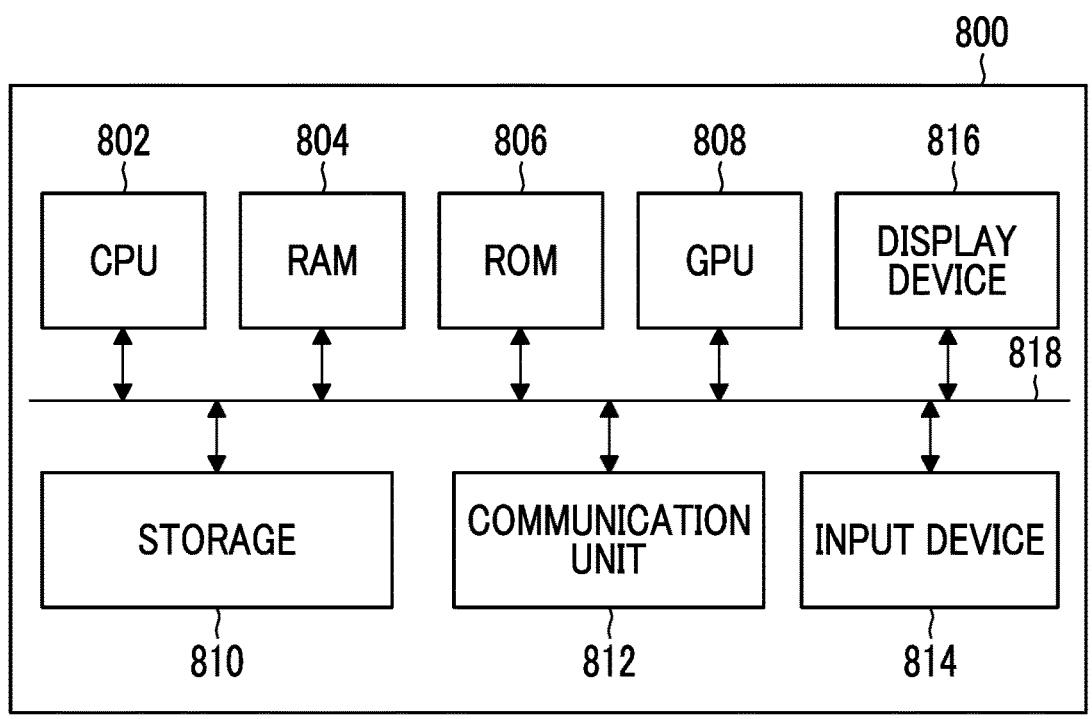
FIG. 14 is a block diagram showing an example of a hardware configuration of a computer.

FIG. 14 is a block diagram showing an example of a hardware configuration of a computer. A computer 800 may be a personal computer, a workstation, or a server computer. The computer 800 may be used as a part or all of the terminal 20, the integration server 30, the DICOM server 22, the electronic medical record system 24, the AI server 60, and the terminal 62 described above, or may be used as an apparatus having a plurality of functions thereof.

The computer 800 comprises a central processing unit (CPU) 802, a random access memory (RAM) 804, a read only memory (ROM) 806, a graphics processing unit (GPU) 808, a storage 810, a communication unit 812, an input device 814, a display device 816, and a bus 818. The GPU 808 may be provided as necessary.

The CPU 802 reads out various programs stored in the ROM 806, the storage 810, or the like, and executes various processing. The RAM 804 is used as a work area of the CPU 802. Further, the RAM 804 is used as a storage unit for temporarily storing the read program and various pieces of data.

The storage 810 includes, for example, a hard disk apparatus, an optical disk, a magneto-optical disk, a semiconductor memory, or a storage device configured by using an appropriate combination thereof. The storage 810 stores various programs, data, and the like required for inference processing and/or learning processing. The program stored in the storage 810 is loaded into the RAM 804, and the CPU 802 executes the program. Thus, the computer 800 functions as units for performing various processing defined by the program.

The communication unit 812 is an interface that performs communication processing with an external apparatus in a wired manner or a wireless manner and that exchanges information with the external apparatus. The communication unit 812 may play a role of an information acquisition unit that receives an input such as an image.

The input device 814 is an input interface that receives various operation inputs to the computer 800. The input device 814 is configured with, for example, a keyboard, a mouse, a touch panel, another pointing device, a voice input device, or an appropriate combination thereof.

The display device 816 is an output interface for displaying various pieces of information. The display device 816 is configured with, for example, a liquid crystal display, an organic electro-luminescence (OEL) display, a projector, or an appropriate combination thereof.

<<Program for Operating Computer>>

A program causing a computer to realize some or all of at least one processing function among various processing functions, such as a data search function, a data collection function, and a local learning function in each terminal 20 and a data collection program setting OF function, a search condition setting function, a learning data distribution function, and a master model learning management function including a master model candidate creation function and an inference accuracy evaluation function in the integration server 30, which are described in the above embodiment, may be recorded on a computer-readable medium as a non-transitory tangible information storage medium, such as an optical disk, a magnetic disk, or a semiconductor memory, and the program may be provided with the information storage medium.

Further, instead of the form in which the program is provided by being stored in such a non-transitory tangible computer-readable medium, a program signal may be provided as a download service using a telecommunication line such as the Internet.

A service may be possible in which some or all of at least one processing function among various processing functions, such as the data search function, the data collection function, and the local learning function in each terminal 20 and the data collection program setting I/F function, the search condition setting function, the learning data distribution function, and the master model learning management function including the master model candidate creation function and the inference accuracy evaluation function in the integration server 30, which are described in the above embodiment, are provided as an application server and the processing function is provided via a telecommunication line.

<<Hardware Configuration of Each Processing Unit>>

Hardware structures of processing units that execute various pieces of processing, such as the search condition input receiving unit 321, the setting file generation unit 322, the totalization result acquisition unit 323, the learning data number distribution unit 324, the notification setting input receiving unit 325, the notification determination unit 326, the addition instruction receiving unit 327, the additional generation distribution unit 328, the learned weight parameter acquisition unit 341, the parameter integration unit 342, and the model update unit 343 shown in FIG. 5 and the search condition setting file acquisition unit 221, the data search unit 222, the search result storage unit 223, the totalization result transmission processing unit, 224, the distribution information acquisition unit 225, the additional generation processing unit 226, the synchronization processing unit 251, the learning data acquisition unit 252, the local model to be trained LM, the error calculation unit 254, the optimizer 255, the learning result storage unit 256, and the learning result transmission processing unit 257 shown in FIG. 9, are various processors as shown below, for example.

The various processors include a CPU which is a general-purpose processor that functions as various processing units by executing a program, a GPU which is a processor specialized for image processing, a programmable logic device (PLD) such as a field programmable gate array (FPGA) which is a processor capable of changing a circuit configuration after manufacture, a dedicated electric circuit such as an application specific integrated circuit (ASIC) which is a processor having a circuit configuration specifically designed to execute specific processing, and the like.

One processing unit may be configured by one of these various processors or may be configured by two or more processors having the same type or different types. For example, one processing unit may be configured by a plurality of FPGAs, a combination of a CPU and an FPGA, or a combination of a CPU and a GPU. Further, the plurality of processing units may be configured by one processor. As an example in which the plurality of processing units are configured by one processor, firstly, as represented by a computer such as a client and a server, a form in which one processor is configured by a combination of one or more CPUs and software and in which the processor functions as the plurality of processing units may be adopted. Secondly, as represented by a system on chip (SoC) or the like, a form in which a processor that realizes the function of the entire system including the plurality of processing units via one integrated circuit (IC) chip is used may be adopted. As described above, the various processing units are configured by using one or more various processors as a hardware structure.

Further, as the hardware structure of the various processors, more specifically, an electric circuit (circuitry) in which circuit elements such as semiconductor elements are combined may be used.

Advantages According to Present Embodiment

With the machine learning system 10 according to the embodiment of the present invention, the following advantages are obtained.

[1] Learning can be performed without extracting personal information, such as a diagnosis image, that requires consideration for privacy from a medical institution to the outside.

[2] It is possible to search for and collect the data used for learning from within the medical institution system MS or to additionally generate new data in a case where the learning data is insufficient.

[3] A mechanism is provided in which the development entity 80 can control the type and number of pieces of data used for local learning at each medical institution while ascertaining the data possession situation of each medical institution. Accordingly, it is possible to suppress a variation in the data used for learning and thus suppress a variation in the inference accuracy of the AI model created by the learning.

Modification Example 1

In the embodiment, the AI model for medical image diagnosis has been described as an example. However, the scope of application of the technique of the present disclosure is not limited to this example. For example, the present disclosure may be applied even in a case where learning is performed on an AI model using time-series data as input data or on an AI model using document data as input data. The time-series data may be, for example, electrocardiogram waveform data. The document data may be, for example, a diagnostic report, and the present disclosure may be applied to training of an AI model for supporting creation of a report. The electrocardiogram waveform data is an example of "inspection data" in the present disclosure.

The data used for learning may be a combination of different kinds of data acquired by different modalities. The data used for the learning may be a combination of a plurality of types of different kinds of data, such as a combination of images and time-series data or a combination of images and document data.

Modification Example 2

In the embodiment, an example in which an accuracy target value by learning is set and the inference accuracy of the master model candidate is compared with the accuracy target value has been described. However, the accuracy target value may be updated as necessary. Instead of or in combination with the comparison with the accuracy target value, the learning may proceed under a condition that the inference accuracy of the model is maximized within the time limit or the designated number of iterations.

<<Other>>

The matters described in the configuration and the modification example described in the embodiment may be used in combination as appropriate, and some matters may be replaced. The present invention is not limited to the embodiment described above, and various modifications may be made without departing from the scope of the present invention.

EXPLANATION OF REFERENCES

10: machine learning system
20: terminal
22: DICOM server
24: electronic medical record system
26: delivered AI model
30: integration server
32: data collection program setting interface
50: medical institution network
52: CT apparatus
54: MM apparatus
56: CR apparatus
60: AI server
62: terminal
66: internal communication line
70: wide area communication line
80: development entity 202: processor
204: computer-readable medium
206: communication interface
208: input/output interface
210: bus
214: input device
216: display device
220: data collection program
221: search condition setting file acquisition unit
222: data search unit
223: search result storage unit
224: totalization result transmission processing unit
225: distribution information acquisition unit
226: additional generation processing unit
250: local learning management program
251: synchronization processing unit
252: learning data acquisition unit
254: error calculation unit
255: optimizer
256: learning result storage unit
257: learning result transmission processing unit
260: display control program
280: learning data storage unit
302: processor
304: computer-readable medium
306: communication interface
308: input/output interface
310: bus
314: input device
316: display device
320: data collection program setting I/F program
321: search condition input receiving unit
322: setting file generation unit
323: totalization result acquisition unit
324: learning data number distribution unit
325: notification setting input receiving unit
326: notification determination unit
327: addition instruction receiving unit
328: additional generation distribution unit
330: synchronization program
340: master model learning management program
341: learned weight parameter acquisition unit
342: parameter integration unit
343: model update unit
350: display control program
360: database
800: computer
802: CPU
804: RAM
806: ROM
808: GPU
810: storage
812: communication unit
814: input device
816: display device
818: bus
LM: local model to be trained
MM: master model to be trained
MS: medical institution system
S11 to S48: processing steps by data collection program setting I/F program
S51 to S62: processing steps by data collection program
S71 to S75: processing steps by local learning management program
S81 to S88: processing steps by master model learning management program
S91 to S94: steps of inference accuracy evaluation processing

What is claimed is:

1. A machine learning system comprising:
a plurality of client terminals; and
an integration server,
wherein each of the plurality of client terminals is a terminal installed in a medical institution system of each of a plurality of medical institutions,
each of the client terminals includes
a first processor, and
a first computer-readable medium on which a first program executed by the first processor is recorded,
the first processor performs, according to a command of the first program, processing including
acquiring a search condition of data from the integration server,
searching for data that matches the search condition from within the medical institution system to which the client terminal belongs and totaling search results,
transmitting a totalization result indicating the number of pieces of the data that matches the search condition to the integration server,
receiving distribution information in which a type and the number of pieces of learning data used for learning at the client terminal are designated,
executing machine learning of a local model to be trained in accordance with an instruction of the distribution information using data in the medical institution system to which the client terminal belongs as the learning data, and
transmitting a learning result of the local model to the integration server,
the integration server includes
a second processor, and
a second computer-readable medium on which a second program executed by the second processor is recorded, and
the second processor performs, according to a command of the second program, processing including
storing a master model to be trained on the second computer-readable medium,
receiving an input that designates the search condition in a case where the data in the medical institution system is searched for,
transmitting the designated search condition to the plurality of client terminals,
receiving the totalization result indicating the number of pieces of the data that matches the search condition from each of the client terminals,
receiving an input that designates the required number of pieces of learning data to be used for learning,
distributing the number of pieces of the learning data used for learning at each of the client terminals based on the designated required number of pieces of the learning data and on the received totalization result,
transmitting, to each of the client terminals, the distribution information including the designation of the number of pieces of the learning data distributed according to each of the client terminals,
synchronizing the local model of each client terminal side with the master model before the local model is trained at each of the plurality of client terminals,
receiving each of the learning results from the plurality of client terminals, and integrating the received learning results to update the master model.

2. The machine learning system according to claim 1 wherein the second processor further issues a notification notifying that the required number is satisfied at a stage where a total number of pieces of the data that matches the search condition is equal to or larger than the required number.

3. The machine learning system according to claim 1, wherein the first processor has authority to execute a third program that generates new secondary data using primary data in the medical institution system, the second processor performs, in a case where a total number of pieces of the data that matches the search condition is less than the required number and the data that matches the search condition is obtainable by operating the third program, processing including distributing the number of pieces of additional data requesting additional data generation to each of the client terminals, and transmitting, to each of the client terminals, additional generation distribution information including designation of the number of pieces of the additional data distributed according to each of the client terminals, and the first processor executes the third program based on the additional generation distribution information to newly generate the secondary data.

4. The machine learning system according to claim 3, wherein the first processor starts training of the local model in a case where the generation of the secondary data of the designated number of pieces of the additional data is completed.

5. The machine learning system according to claim 3, wherein the third program includes a trained model in which the secondary data is output by inputting the primary data.

6. The machine learning system according to claim 1, wherein each of the plurality of client terminals is a terminal installed in a medical institution network of a different medical institution.

7. The machine learning system according to claim 1, wherein the integration server is installed in a medical institution network or outside the medical institution network.

8. The machine learning system according to claim 1, wherein the learning result transmitted from the client terminal to the integration server includes a weight parameter of the local model after learning.

9. The machine learning system according to claim 1, wherein data to be searched for by the search condition includes at least one type of data of a two-dimensional image, a three-dimensional image, a moving image, time-series data, or document data.

10. The machine learning system according to claim 9, wherein the document data includes comments on findings of an electronic medical record.

11. The machine learning system according to claim 1, wherein models to be trained of each of the local model and the master model are trained such that comments on findings corresponding to an input image are output, using a combination of an image and comments on findings associated with the image as the learning data.

12. The machine learning system according to claim 1, wherein models to be trained of each of the local model and the master model are configured by using a neural network.

13. The machine learning system according to claim 1, wherein the data used as the learning data includes a two-dimensional image, a three-dimensional image, or a moving image, and models to be trained of each of the local model and the master model are configured by using a convolutional neural network.

14. The machine learning system according to claim 1, wherein the data used as the learning data includes time-series data or document data, and models to be trained of each of the local model and the master model are configured by using a recurrent neural network.

15. A machine learning method in which a plurality of client terminals and an integration server are used, the method comprising:

via each of the plurality of client terminals, which are installed in a medical institution system of each of a plurality of medical institutions, storing a master model to be trained in the integration server;

via the integration server, receiving an input that designates a search condition in a case where data in the medical institution system is searched for; and transmitting the designated search condition to the plurality of client terminals;

via the client terminal, acquiring the search condition from the integration server;

searching for data that matches the search condition from within the medical institution system to which the client terminal belongs and totaling search results; and transmitting a totalization result indicating the number of pieces of the data that matches the search condition to the integration server;

via the integration server, receiving the totalization result indicating the number of pieces of the data that matches the search condition from each of the client terminals;

receiving an input that designates the required number of pieces of learning data to be used for learning;

distributing the number of pieces of the learning data used for learning at each of the client terminals based on the designated required number of pieces of the learning data and on the received totalization result;

transmitting, to each of the client terminals, the distribution information including the designation of the number of pieces of the learning data distributed according to each of the client terminals; and synchronizing the local model of each client terminal side with the master model before the local model is trained at each of the plurality of client terminals;

via the client terminal, receiving the distribution information in which a type and the number of pieces of learning data used for learning at the client terminal are designated;

executing machine learning of a local model to be trained in accordance with an instruction of the distribution information using data in the medical institution system to which the client terminal belongs as the learning data; and transmitting a learning result of the local model to the integration server; and via the integration server, receiving each of the learning results from the plurality of client terminals; and integrating the received learning results to update the master model.

16. An information processing apparatus that is used as a client terminal connected to an integration server via a communication line and is a terminal installed in a medical institution system of a medical institution, the information processing apparatus comprising:
- a first processor; and
- a first computer-readable medium on which a first program executed by the first processor is recorded,
- wherein the first processor performs, according to a command of the first program, processing including
  - acquiring a search condition of data from the integration server,
  - searching for data that matches the search condition from within the medical institution system to which the client terminal belongs and totaling search results,
  - transmitting a totalization result indicating the number of pieces of the data that matches the search condition to the integration server,
  - receiving distribution information in which a type and the number of pieces of learning data used for learning at the client terminal are designated,
  - executing machine learning of a local model to be trained in accordance with an instruction of the distribution information using data in the medical institution system to which the client terminal belongs as the learning data, and
  - transmitting a learning result of the local model to the integration server.

17. A non-transitory, computer readable tangible recording medium which records thereon a program for causing a first computer to function as a client terminal connected to an integration server via a communication line, the program causing the first computer to realize:
- a function of acquiring a search condition of data from the integration server;
- a function of searching for data that matches the search condition from within a medical institution system to which the client terminal belongs and totaling search results;
- a function of transmitting a totalization result indicating the number of pieces of the data that matches the search condition to the integration server;
- a function of receiving distribution information in which a type and the number of pieces of learning data used for learning at the client terminal are designated;
- a function of executing machine learning of a local model to be trained in accordance with an instruction of the distribution information using data in the medical institution system to which the client terminal belongs as the learning data; and
- a function of transmitting a learning result of the local model to the integration server.

18. An integration server connected to a plurality of client terminals via a communication line, the integration server comprising:
- a second processor; and
- a second computer-readable medium on which a second program executed by the second processor is recorded,
- wherein the second processor performs, according to a command of the second program, processing including
  - storing a master model to be trained on the second computer-readable medium,
  - receiving an input that designates a search condition in a case where data in a medical institution system to which each of the plurality of client terminals belongs is searched for,
  - transmitting the designated search condition to the plurality of client terminals,
  - receiving a totalization result indicating the number of pieces of the data that matches the search condition from each of the client terminals,
  - receiving an input that designates the required number of pieces of learning data to be used for learning,
  - distributing the number of pieces of the learning data used for learning at each of the client terminals based on the designated required number of pieces of the learning data and on the received totalization result,
  - transmitting, to each of the client terminals, distribution information including the designation of the number of pieces of the learning data distributed according to each of the client terminals,
  - synchronizing a local model of each client terminal side with the master model before the local model is trained at each of the plurality of client terminals,
  - receiving a learning result of each of the local models from the plurality of client terminals, and
  - integrating the received learning results to update the master model.

19. A non-transitory, computer readable tangible recording medium which records thereon a program for causing a second computer to function as an integration server connected to a plurality of client terminals via a communication line, the program causing the second computer to realize:
- a function of storing a master model to be trained;
- a function of receiving an input that designates a search condition in a case where data in a medical institution system to which each of the plurality of client terminals belongs is searched for;
- a function of transmitting the designated search condition to the plurality of client terminals;
- a function of receiving a totalization result indicating the number of pieces of the data that matches the search condition from each of the client terminals;
- a function of receiving an input that designates the required number of pieces of learning data to be used for learning;
- a function of distributing the number of pieces of the learning data used for learning at each of the client terminals based on the designated required number of pieces of the learning data and on the received totalization result;
- a function of transmitting, to each of the client terminals, distribution information including the designation of the number of pieces of the learning data distributed according to each of the client terminals;
- a function of synchronizing a local model of each client terminal side with the master model before the local model is trained at each of the plurality of client terminals;
- a function of receiving a learning result of each of the local models from the plurality of client terminals; and
- a function of integrating the received learning results to update the master model.

20. A method of creating an inference model by performing the machine learning method according to claim 15, the method comprising creating, by integrating the received learning results to update the master model, an inference model having higher inference accuracy than the master model before the update.

* * * * *